US011937976B2

United States Patent
Eibl et al.

(10) Patent No.: US 11,937,976 B2
(45) Date of Patent: Mar. 26, 2024

(54) ULTRASOUND PATCH WITH INTEGRATED FLEXIBLE TRANSDUCER ASSEMBLY

(71) Applicants: 1929803 ONTARIO CORP., Sudbury (CA); Joseph Eibl, Sudbury (CA); Andrew Eibl, Sudbury (CA); Jon-Emile S. Kenny, Sudbury (CA)

(72) Inventors: Joseph Eibl, Sudbury (CA); Kyle Fredericks, Sudbury (CA); Chelsea Munding, Sudbury (CA); Andrew Eibl, Sudbury (CA); Jon-Emile S. Kenny, Sudbury (CA)

(73) Assignee: 1929803 Ontario Corp, Sudbury (CA)

( * ) Notice: Subject to any disclaimer, the term of this patent is extended or adjusted under 35 U.S.C. 154(b) by 288 days.

(21) Appl. No.: 17/368,333

(22) Filed: Jul. 6, 2021

(65) Prior Publication Data

US 2022/0000447 A1 Jan. 6, 2022

Related U.S. Application Data

(60) Provisional application No. 63/048,437, filed on Jul. 6, 2020.

(51) Int. Cl.
*A61B 8/00* (2006.01)
*B06B 1/06* (2006.01)
*A61B 8/08* (2006.01)

(52) U.S. Cl.
CPC .......... *A61B 8/4236* (2013.01); *A61B 8/4281* (2013.01); *A61B 8/4483* (2013.01); *B06B 1/0622* (2013.01); *A61B 8/488* (2013.01)

(58) Field of Classification Search
CPC ............................ A61B 8/4236; A61B 8/4483
See application file for complete search history.

(56) References Cited

U.S. PATENT DOCUMENTS

| | | |
|---|---|---|
| 4,103,679 A | 8/1978 | Aronson |
| 4,189,655 A | 2/1980 | Bruel |
| | (Continued) | |

FOREIGN PATENT DOCUMENTS

| | | |
|---|---|---|
| CA | 2950919 A1 | 1/2016 |
| CN | 102046222 A | 5/2011 |
| | (Continued) | |

OTHER PUBLICATIONS

Blanco et al., "Rapid Ultrasound in Shock (RUSH) Velocity-Time Integral", J Ultrasound Med., vol. 34, pp. 1691-1700, Aug. 2015.

(Continued)

*Primary Examiner* — Angela M Hoffa
*Assistant Examiner* — Younhee Choi
(74) *Attorney, Agent, or Firm* — Perkins Coie LLP

(57) ABSTRACT

A self-contained ultrasound patch assembly for detecting fluid flow in a vessel includes piezo elements that can transmit ultrasonic energy and detect echo signals. A flex module has two support portions connected to respective ones of the elements with a hinged portion coupled to the support portions, allowing them to be positioned angularly relative to each other. Electronics that direct the elements to transmit ultrasonic energy and process detected echo signals are in communication with the elements through the flex module. A transducer frame includes an alignment portion engaging a flex module alignment portion to retain the flex module in an aligned position. The frame supports the elements at a fixed angular position with respect to each other. A housing encloses the electronics and frame, and fixedly retains the frame to position the elements to transmit toward a bottom surface and away from a top surface of the housing.

18 Claims, 14 Drawing Sheets

(56) References Cited

U.S. PATENT DOCUMENTS

| | | | |
|---|---|---|---|
| 5,113,867 A | 5/1992 | Janszen | |
| 5,390,675 A * | 2/1995 | Sheehan | A61B 8/4281 |
| | | | 600/459 |
| 6,142,946 A | 11/2000 | Hwang et al. | |
| 8,876,720 B2 | 11/2014 | Vezina | |
| 10,394,209 B2 | 8/2019 | Goodon et al. | |
| 10,661,009 B2 | 5/2020 | Eibl et al. | |
| 10,912,534 B2 | 2/2021 | Eibl et al. | |
| 10,987,085 B2 | 4/2021 | Eibl et al. | |
| 11,109,831 B2 | 9/2021 | Eibl et al. | |
| 11,324,476 B2 | 5/2022 | Eibl et al. | |
| 11,511,040 B2 | 11/2022 | Eibl et al. | |
| 2001/0021817 A1 | 9/2001 | Brugger et al. | |
| 2002/0042574 A1 | 4/2002 | Manor et al. | |
| 2004/0138568 A1 | 7/2004 | Lo et al. | |
| 2005/0020919 A1 | 1/2005 | Stringer et al. | |
| 2005/0156491 A1 | 7/2005 | Scott | |
| 2005/0245827 A1 | 11/2005 | Takeda et al. | |
| 2006/0135940 A1 | 6/2006 | Joshi | |
| 2006/0206032 A1 | 9/2006 | Miele et al. | |
| 2006/0264756 A1 | 11/2006 | Lo et al. | |
| 2007/0016046 A1 | 1/2007 | Mozayeni et al. | |
| 2008/0208273 A1 | 8/2008 | Owen et al. | |
| 2009/0221948 A1 | 9/2009 | Szamosfalvi et al. | |
| 2010/0016725 A1 | 1/2010 | Thiele | |
| 2010/0022886 A1 | 1/2010 | Ayati et al. | |
| 2010/0049052 A1 | 2/2010 | Sharf et al. | |
| 2010/0076315 A1 | 3/2010 | Erkamp et al. | |
| 2010/0160784 A1 | 6/2010 | Poland et al. | |
| 2011/0137173 A1 | 6/2011 | Lowe et al. | |
| 2011/0319766 A1 | 12/2011 | Tsuruno | |
| 2012/0095352 A1 | 4/2012 | Tran | |
| 2012/0138533 A1 | 6/2012 | Curtis et al. | |
| 2012/0184854 A1 | 7/2012 | Raju et al. | |
| 2012/0197118 A1 | 8/2012 | Lisiecki et al. | |
| 2012/0277640 A1 | 11/2012 | Lewis, Jr. et al. | |
| 2012/0296216 A1 | 11/2012 | Sharf et al. | |
| 2013/0116571 A1 | 5/2013 | Cox et al. | |
| 2013/0144166 A1 | 6/2013 | Specht et al. | |
| 2014/0058259 A1 | 2/2014 | Liu | |
| 2014/0081144 A1 | 3/2014 | Moehring et al. | |
| 2014/0163374 A1 | 6/2014 | Ogasawara et al. | |
| 2014/0371594 A1 | 12/2014 | Flynn et al. | |
| 2015/0009782 A1 | 1/2015 | Engl et al. | |
| 2015/0135840 A1 | 5/2015 | Sato et al. | |
| 2015/0272513 A1 | 10/2015 | Tan et al. | |
| 2015/0289838 A1 | 10/2015 | Nichol et al. | |
| 2015/0335820 A1 | 11/2015 | De Armond et al. | |
| 2016/0206292 A1 | 7/2016 | Vezina | |
| 2016/0351783 A1 | 12/2016 | Chang et al. | |
| 2017/0049413 A1 | 2/2017 | Nichol et al. | |
| 2017/0080255 A1 | 3/2017 | Law et al. | |
| 2017/0105700 A1 | 4/2017 | Bar-zion et al. | |
| 2017/0110504 A1 | 4/2017 | Panchawagh et al. | |
| 2017/0293277 A1 | 10/2017 | Goodon et al. | |
| 2017/0325328 A1 | 11/2017 | Isaac et al. | |
| 2017/0332995 A1 | 11/2017 | Eibl et al. | |
| 2018/0020982 A1 | 1/2018 | Elsherbini et al. | |
| 2018/0092621 A1 * | 4/2018 | Duerr | A61B 8/4477 |
| 2018/0206819 A1 | 7/2018 | Saarinen et al. | |
| 2018/0353157 A1 | 12/2018 | Eibl et al. | |
| 2019/0021659 A1 | 1/2019 | Sajwan et al. | |
| 2019/0022400 A1 | 1/2019 | Kumar et al. | |
| 2019/0059848 A1 | 2/2019 | Owen et al. | |
| 2020/0022670 A1 | 1/2020 | Eibl et al. | |

FOREIGN PATENT DOCUMENTS

| | | | | |
|---|---|---|---|---|
| CN | 102333486 A | 1/2012 | | |
| CN | 102871645 A | 1/2013 | | |
| CN | 104883967 A | 9/2015 | | |
| CN | 110871158 A * | 3/2020 | | A61B 8/085 |
| FR | 2585944 A1 | 2/1987 | | |
| JP | S58118739 A | 7/1983 | | |
| JP | S62501682 A | 7/1987 | | |
| JP | H05347797 A | 12/1993 | | |
| JP | H07124159 A | 5/1995 | | |
| JP | 2002541899 A | 12/2002 | | |
| JP | 2004344564 A | 12/2004 | | |
| JP | 2008534071 A | 8/2008 | | |
| JP | 2008259850 A | 10/2008 | | |
| JP | 2009515439 A | 4/2009 | | |
| JP | 2009524467 A | 7/2009 | | |
| JP | 2010504829 A | 2/2010 | | |
| JP | 2012005690 A | 1/2012 | | |
| JP | 2012518454 A | 8/2012 | | |
| JP | 2013078570 A | 5/2013 | | |
| JP | 2014503239 A | 2/2014 | | |
| JP | 2014054580 A | 3/2014 | | |
| JP | 2014168603 A | 9/2014 | | |
| JP | 2015130520 A | 7/2015 | | |
| JP | 2017528940 A | 9/2017 | | |
| WO | 8604225 A1 | 7/1986 | | |
| WO | 0062677 A1 | 10/2000 | | |
| WO | 2006030354 A1 | 3/2006 | | |
| WO | 2006102511 A2 | 9/2006 | | |
| WO | 2007085999 A1 | 8/2007 | | |
| WO | 2008042559 A2 | 4/2008 | | |
| WO | 2008124644 | 10/2008 | | |
| WO | 2009154298 A1 | 12/2009 | | |
| WO | 2010097728 A1 | 9/2010 | | |
| WO | 2015074015 A1 | 5/2015 | | |
| WO | 2015181167 A1 | 12/2015 | | |
| WO | 2015184073 A1 | 12/2015 | | |
| WO | 2017096487 A1 | 6/2017 | | |
| WO | 2018102911 A1 | 6/2018 | | |

OTHER PUBLICATIONS

Chinese Office Action in Chinese Application No. 201680071647.0; dated Mar. 24, 2021; 18 pages.

EPO, Extended European Search Report, EP Patent Application 19763312.6, dated Oct. 18, 2021, 9 pages.

EPO, Extended European Search Report, EP Patent Application 19838308.5, dated Mar. 14, 2022, 9 pages.

European Patent Office, extended European search report for European Application No. 16871876.5; dated Sep. 20, 2019; 36 pages.

International Search Report and Written Opinion for International Application No. PCT/CA2016/051451; dated Mar. 14, 2017; 10 pages.

International Search Report and Written Opinion for International Application No. PCT/CA2017/050714; dated Mar. 2, 2018; 10 pages.

International Search Report and Written Opinion for International Application No. PCT/CA2019/050918; dated Sep. 23, 2019; 11 pages.

Japanese Office Action in Japanese Application No. 2018-0530760; dated Oct. 26, 2020; 6 pages.

International Search Authority, International Search Report and Written Opinion of the International Searching Authority for International Application No. PCT/IB2021/000453, dated Nov. 3, 2021, 10 pages.

Kenny et al., "A novel, hands-free ultrasound patch for continuous monitoring of quantitative Doppler in the carotid artery", Scientific Reports 11, pp. 1-11, Apr. 8, 2021, URL: https://www.nature.com/articles/s41598-021-87116-y.

Guillaume, Mahe, et al., "Statement for Doppler waveforms analysis", Journal of Vascular Diseases, vol. 46, No. 5, Aug. 1, 2017 (Aug. 1, 2017), pp. 337-345, XP55848917, DE, ISSN: 0301-1526, DOI: 10.1024/0301-1526/a000638.

International Search Report, PCT Patent Application PCT/CA2019/050292, dated Jun. 28, 2019, 8 pages.

* cited by examiner

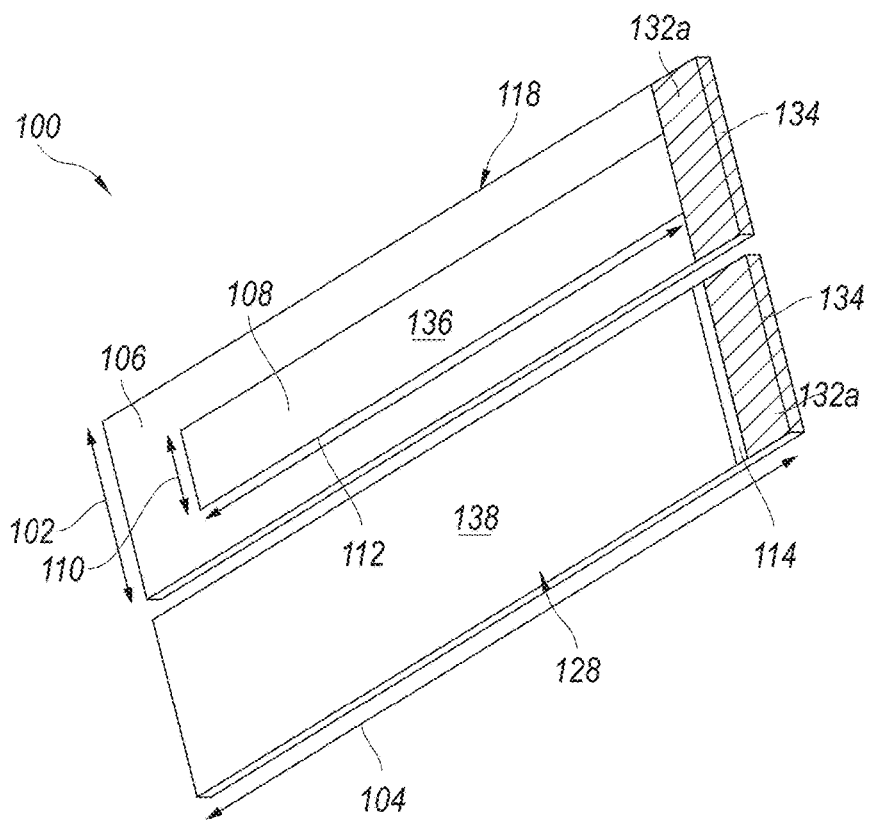
FIG. 2A
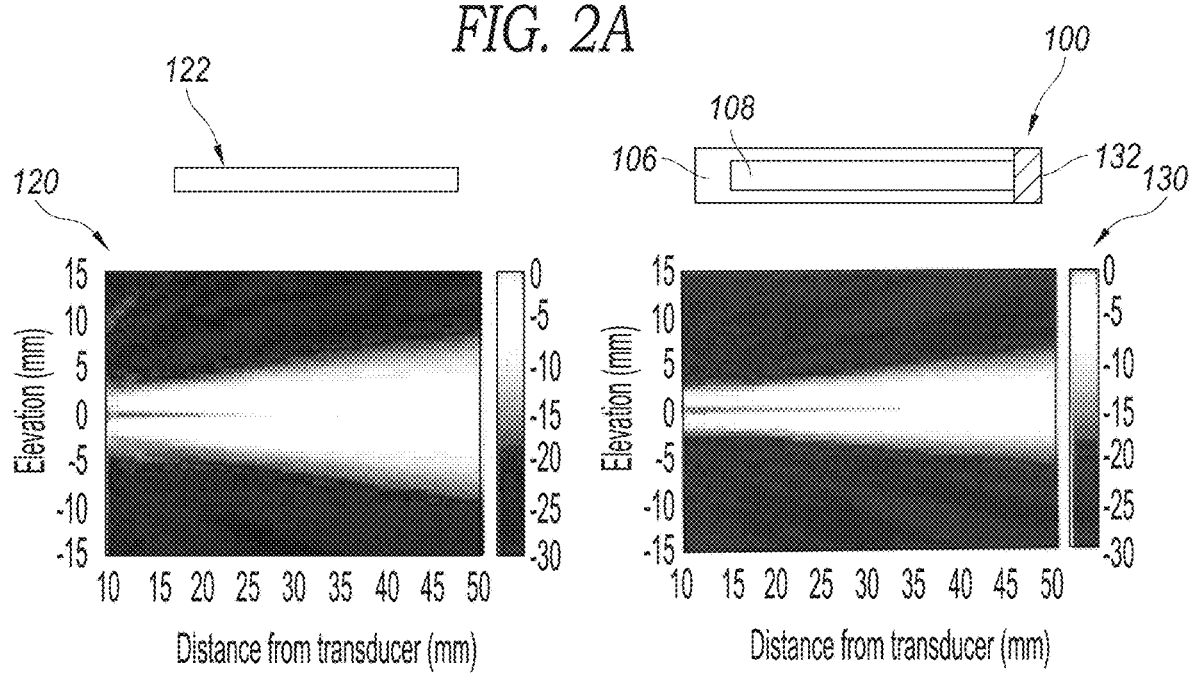
FIG. 2B
FIG. 2C

ULTRASOUND PATCH WITH INTEGRATED FLEXIBLE TRANSDUCER ASSEMBLY

CROSS-REFERENCE TO RELATED APPLICATIONS

This application claims the benefit of U.S. Provisional Patent Application No. 63/048,437 filed Jul. 6, 2020, which is incorporated herein by reference in its entirety.

TECHNICAL FIELD

The disclosed technology relates to ultrasound devices designed to detect fluid flow in a vessel.

BACKGROUND

In many clinical and diagnostic settings, physicians or other medical personnel often use ultrasound to assess how well blood is flowing through a subject's vasculature. Many ultrasound systems require that an operator use one hand to hold an ultrasound transducer at a particular angle to a vessel while using the other hand to control a base unit of the ultrasound imaging system, thereby preventing the performance of other tasks while measuring flow. Other ultrasound transducer devices can be affixed to a subject to continuously or periodically measure flow in a vessel, thereby freeing up the hands of the caregiver. An example of an ultrasound patch for detecting and measuring fluid flow in a vessel that provided a significant advancement is described in U.S. patent application Ser. No. 16/377,028, filed Apr. 5, 2019, (published as U. S. 2020-0022670 A1), which is incorporated herein by reference in its entirety.

The disclosed technology relates to improvements in the design of the ultrasound transducer devices that can be affixed to a subject.

BRIEF DESCRIPTION OF THE DRAWINGS

FIG. 2A shows front and rear surfaces of a single ceramic piezo element that can be used within the ultrasound patch assembly of FIG. 1 to transmit and/or receive signals.

FIGS. 2B and 2C show example heat maps that illustrate the difference in the geometric broadening of the Doppler signal between two piezo elements that have different sized active areas in accordance with embodiments of the present technology.

Figure 1:
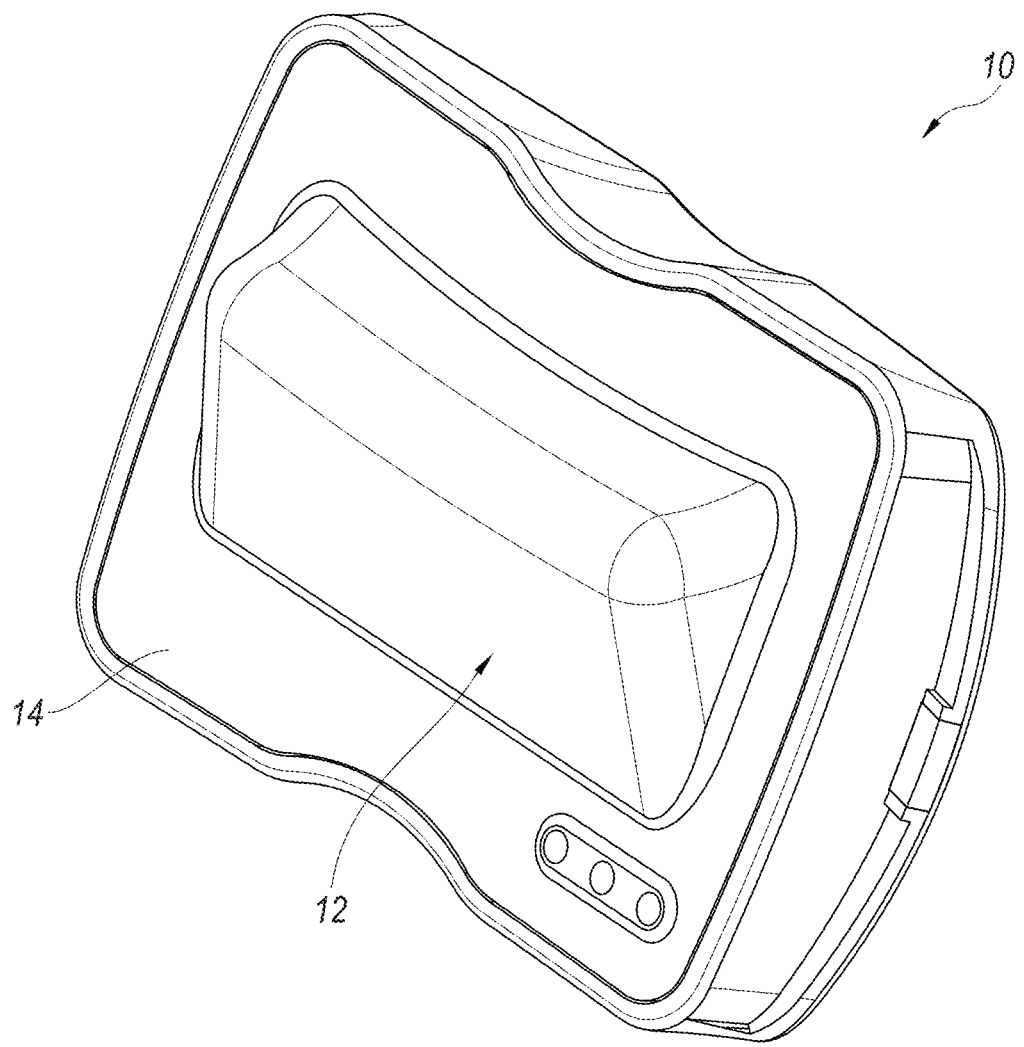
FIG. 1 shows an ultrasound patch assembly in accordance with embodiments of the present technology.

The techniques introduced herein may be better understood by referring to the following Detailed Description in conjunction with the accompanying drawings, in which like reference numerals indicate identical or functionally similar elements. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

The disclosed technology relates to an improved ultrasound patch assembly (e.g., transducer) with a frame-mounted flexible transducer assembly configured to detect flow in a vessel (e.g., artery, vein, etc.). The ultrasound patch assembly includes the electronics, power source (e.g., battery), circuit board(s), memories, antenna, speaker, etc., within a housing to form a self-contained unit that transmits ultrasound waves, detects ultrasound echoes, processes data, and communicates wirelessly and/or through a cable with one or more other devices. As will be discussed in detail below, the ultrasound patch assembly includes air-backed piezoelectric elements ("piezo elements") that produce ultrasonic waves (e.g., ultrasonic energy) for delivery towards a vessel and produce electronic signals from the corresponding acoustic echo signals that are received. In some embodiments, the base or patient interfacing side of the patch assembly is wedge-shaped and configured to fit into a notch or recess in the subject's neck below the jaw and to the side of the trachea to position the transducer piezo elements as close as possible to acquire ultrasonic data associated with the carotid and/or jugular vessels. The patient interfacing side of the patch can have other shapes and be configured to image flow in other anatomy.

In some embodiments, the ultrasound patch assembly configured for use on the skin of a patient to detect fluid flow in a vessel in the patient includes two piezoelectric (piezo) elements that can transmit ultrasonic energy and detect echo signals. A flex module has first and second support portions connected to a respective one of the piezo elements and includes a hinged portion coupled to the first and second support portions configured to allow the first and second support portions to be positioned angularly relative to each other. The flex module also includes a first alignment portion. Electronics are in communication with the two piezo elements through the flex module, and the electronics are configured to direct the two piezo elements to transmit the ultrasonic energy as well as to process the detected echo signals. A transducer frame includes a second alignment portion that engages the first alignment portion of the flex module to retain the flex module in an aligned position on the transducer frame. The transducer frame supports the two piezo elements at a fixed angular position with respect to each other. A housing encloses the electronics and the transducer frame within an interior area. The housing includes a top surface opposite a bottom surface. During use with the patient, the top surface faces away from the skin of the patient and the bottom surface faces toward the skin of the patient. The housing fixedly retains the transducer frame and the flex module to position the two piezo elements to transmit the ultrasonic energy toward the bottom surface and away from the top surface.

In other embodiments, the ultrasound patch assembly configured for use on the skin of a patient to detect fluid flow in a vessel in the patient includes piezo elements that have front and rear surfaces and that are configured to transmit ultrasonic energy and detect echo signals. A flex module includes support portions connected to electrodes with conductive material. First and second support portions and a hinged portion that is coupled to the first and second support portions to allow the first and second support portions to be positioned angularly relative to each other. Electrodes are positioned on the first and second support portions. The conductive material electrically interconnects the rear surfaces of associated ones of the piezo elements and the electrodes. An air gap is formed between portions of the piezo elements and electrode-free portions of the first and second support portions. A transducer frame includes first and second surfaces that receive the first and second support portions of the flex module. The first and second surfaces have an angular arrangement to position the piezo elements at one of a plurality of angles relative to each other, and a retention element engages at least one of the piezo elements to retain the first and second support portions of the flex module relative to the first and second surfaces of the transducer frame. A housing includes a top shell and base. The top shell has a top surface configured to face away from the skin of the patient. The base has a bottom surface that is opposite the top surface of the top shell that is configured to face toward the skin of the patient during use with the patient. The bottom surface of the base includes a central portion that protrudes outwardly to form a cavity within the base, and the transducer frame is partially held within the cavity of the housing to position the piezo elements to transmit the ultrasound energy toward the bottom surface and away from the top surface.

In still further embodiments, an ultrasound patch assembly is configured for use on the skin of a patient to detect fluid flow in a vessel in the patient. The ultrasound patch transducer includes first and second piezo elements and a transducer frame enclosed within a housing. The first and second piezo elements are configured to transmit ultrasonic energy and detect echo signals, and each have front and rear surfaces. The transducer frame is made of a rigid material and has first and second surfaces. Sidewalls extend outwardly from opposite ends of the first and second surfaces. The sidewalls and first and second surfaces form a receiving area for the first and second piezo elements, and the first and second surfaces have an angular arrangement to position the front surfaces of the first and second piezo elements at less than 180 degrees with respect to each other. At least one of the sidewalls includes a retention feature protruding from the sidewall into the receiving area proximate the front surface of at least one of the first and second piezo elements. The housing includes a top surface that faces away from the skin of the patient and a bottom surface opposite the top surface that faces toward the skin of the patient during use with the patient. The housing retains the transducer frame at a fixed position to position the first and second piezo elements to transmit the ultrasonic energy toward the bottom surface and away from the top surface.

A method of manufacturing and/or assembling the self-contained ultrasound patch assembly is also disclosed herein. The manufacturing/assembly process also includes the necessary installation and interconnection of elements discussed previously, such as electronics, power source (e.g., battery), circuit board(s), memories, antenna, speaker, etc., within the same housing as the piezo elements to form a self-contained unit that transmits ultrasound waves, detects ultrasound echoes, processes data, and communicates wirelessly and/or through a cable with one or more other devices and/or networks. The ultrasound patch assembly can include a flexible transducer assembly that has a flexible printed circuit board module fastened to the piezo elements with a z-axis anisotropic conductive tape. The conductive tape interfaces with at least substantially inactive areas of the elements. Two separate piezo elements can be positioned angularly with respect to each other within a selected one of a plurality of transducer frames, and the frame is snapped into a base of the ultrasound patch assembly. The components of the ultrasound patch assembly can be fully assembled inside the base, allowing all parts to be fit together in a systematic and reproducible fashion. The top shell can be attached to the base to provide a secure unit that may be waterproof.

Each of the plurality of transducer frames can receive and retain piezo elements, and each of the transducer frames holds the piezo elements at a different angular orientation with respect to each other than other frames. The angular orientation can be less than 180 degrees such that the ultrasound beams intersect and focus at different imaging depths. In other embodiments, the angular orientation can be 180 degrees or more to direct ultrasound beams and detect echo signals from ultrasound beams that do not intersect. In some embodiments, one or more lenses can be used to change the transmission and/or detection to an angle that is non-normal to a front surface of the piezo element(s). The different transducer frames can be used with the same housing, providing ease and economy in manufacturing/ assembling ultrasound patch assemblies that can be used for different imaging applications and different neck anatomies.

Additionally, several methods are disclosed for acoustically potting the piezo elements in the base. A non-conductive epoxy or other potting material with the desired acoustic properties can be used. The transducer frame and piezo elements can be secured in the base either before or after the potting material is placed in the base. The frame and element configuration provide opening(s) for air bubbles to escape so that the bubbles do not become trapped in the potting material between the elements and the inner surface of the base.

In other embodiments, multiple individual piezo elements in two different arrays can be used instead of the two separate piezo elements. Two arrays of elements can be attached to the stiffened flex module with the z-axis anisotropic conductive tape. The two arrays can be held at an angle with respect to each other in the transducer frame and installed in the same patch assembly housing. In some cases, the stiffened flex module can be flexed or bent to form a curvilinear shaped transducer face to increase the imaging area. In some cases, the ultrasonic information associated with each of the elements in the arrays of elements can be evaluated to identify the elements that are seeing flow. Elements that are imaging tissue and not seeing flow can be turned off, saving power and reducing signal-to-noise ratio (SNR). In some cases, multiple vessels can be imaged simultaneously, and multiple imaging areas may be defined.

FIG. 1 shows an ultrasound patch assembly 10 in accordance with embodiments of the present technology. The ultrasound patch assembly 10 can be a small, self-contained unit that can interface directly with the skin of a patient, with the use of ultrasonic gel or other acoustic coupling medium therebetween, to detect fluid flow. In general, the patch assembly 10 includes transducer piezo elements that direct ultrasound energy (e.g., ultrasound waves) into a subject and receive echo signals from moving body fluids (e.g., blood). A wedge 12 extends outwardly from a skin contacting portion 14 of the patch assembly 10. The wedge 12 is sized to fit into, for example, a notch between the sternocleidomastoid muscle and the trachea to be closer to the carotid artery and the jugular vein of the subject. As discussed further below, the piezo elements are held within the wedge 12 and transmit/receive ultrasound to detect flow within one or more vessels. The ultrasound patch assembly 10 is a self-contained unit that includes, within the housing with the piezo elements, the electronics that direct the piezo elements to transmit the ultrasound energy, and that receive and process electronic signals from the detected echo signals. A power source, such as one or more batteries, antenna or other electronics for transmitting and receiving data to and from other electronic devices and/or networks, memories, speaker, etc., are included within the housing.

FIG. 2A shows front and rear surfaces 118 and 128 of a single ceramic piezo element 100 that can be used within the ultrasound patch assembly 10 of FIG. 1 to transmit and/or receive signals. In some embodiments, the patch assembly 10 includes one piezo element 100 that is configured to transmit ultrasound energy and a second piezo element 100 that is configured to receive ultrasound energy (e.g., detect echo signals). In other embodiments, one or both of the piezo elements 100 can be patterned to form an array of elements.

The piezo element 100 can be made of a rectangular sheet of Lead Zirconate Titanate (PZT) or other piezoelectric ceramic material and has a first dimension 102 (e.g., width) and a second dimension 104 (e.g., length) that define an overall surface area. In some embodiments, the first and second dimensions 102, 104 can be in the range of about 5 millimeters (mm) and 30 mm, respectively, although the elements 100 could be made larger or smaller. In other embodiments, the first dimension 102 can be about 4.86 mm and the second dimension 104 can be about 25.94 mm. An active area 108 is formed on a portion of the piezo element 100 and has first and second dimensions 110, 112 that are smaller than the first and second dimensions 102, 104. In some embodiments, the first and second dimensions 110, 112 of the active area 108 can be in the range of about 2.5 mm and 24 mm, respectively. In other embodiments, the first dimension 110 can be about 2.4 mm and the second dimension 112 can be about 24 mm.

An inactive border 106 is formed along three sides of an outer edge of the piezo element 100 around the active area 108. The border 106 is inactive because it lacks an electrode on the front surface 118, which is uncoated within the area of the border 106. Border area 132a (shown with diagonal lines) is also inactive, but has an electrode applied on the front surface 118.

The active region within the active area 108 can achieve higher and more uniform efficiency across the entire active region compared with a piezo element that is the size of the active area 108 that does not have the inactive border 106, 132. In some embodiments, a smaller portion of the active area 108 (e.g., less than the area defined by first and second dimensions 110, 112) can be designed as an active region.

An electrode 136 (shown in gray) covers the active area 108 and the border area 132. The electrode 136 continues around edge 134 onto the rear surface 128 and ends at channel 114. Because the same, continuous electrode 136 exists on both front and rear surfaces 118, 128 of the piezo element 100, there is no voltage differential. The channel 114 is positioned under one short edge of the active area 108 and can break the electrical connection between the front surface 118 of the piezo element 100 and the rear surface 128.

A bottom surface of the active area 108 (e.g., a subset of rear surface 128) has a ground or signal conductive electrode 138 (shown in gray, that may be formed of, e.g., metallic coating, gold, copper, etc.) patterned onto it electrically to form the active areas of the transmit and/or receive elements. The electrode material can be approximately 10 microns thick or less. In some embodiments, a single transmit or a single receive element is patterned onto the active area 108 of the piezo element 100.

It is desirable for the piezo element 100 to have a configuration that focuses the beam energy as much as possible along the center axis, minimizing side lobe levels. Compared to the beam generated from an active area 108 with dimensions substantially similar to the active area 108 (e.g., the configuration shown in FIG. 2A) but without an inactive border, the larger element 100 with the inactive border 106 results in narrower beam directivity. Because there is less diffraction, more energy is at the center of the beam along the Doppler angle where it is desired and less energy goes to the sides where it would contribute to clutter or noise. Therefore, the doppler SNR is optimized. In some embodiments, the size of the ultrasound beam can be changed or rearranged by adjusting the two-dimensional size of the active area 108.

FIGS. 2B and 2C show example heat maps that illustrate differences in the geometric broadening of the Doppler signal between two different piezo elements. FIG. 2B shows a heat map 120 associated with a piezo element 122 that has an overall surface area that is active and substantially equal in size to the active area 108 of FIG. 2A. In this example, a conductive tape was applied under the surface of the element 122, but the tape conveyed an insufficient amount of energy to excite the entire active area and thus generated significant side lobes. FIG. 2C shows a heat map 130 associated with the piezo element 100 wherein the active area 108 is a subset of the overall surface area. By increasing the overall surface area of the piezo element 100, the conductive tape conveyed enough energy to excite the active area 108. The heat map 130 shows a reduced production of side lobes and a directivity of the beam that results in less geometric broadening of the Doppler signal due to the border 106, 132 forming a continuous, flat surface outside the active area 108.

The front and rear surfaces 118, 128 of the piezo element 100 can be coated with a metal conductor such as gold or gold plus chromium via a sputtering, screen printing, or other deposition process(es). Other conductive metals such as copper or aluminum etc. could also be used. In some embodiments, masking or patterning could be used during the application of the electrode 136 to the front surface 118 to ensure that the electrode 136 is applied only in the "T-shape", and on the rear surface 128 to ensure that the channel 114 is not plated. A PZT sheet (e.g., a sheet that can produce multiple elements 100) can be plated on both flat sides and then tilted and plated on one edge 134 so that there is a continuous electrical path from the front surface 118 to the rear surface 128 via the plated edge 134 as discussed with respect to FIG. 2A. In some embodiments, the channel 114 can be cut on the rear surface 128 with a dicing saw or laser to break the electrical connection on the rear surface 128 so that an electrical connection can be made to both the front and rear surfaces 118, 128 of the piezo element 100 from the rear surface 128. The PZT sheet can then be cut or separated with a dicing saw or a patterning laser to form a number of individual transducer piezo elements 100. Other methods of fabrication may be used.

Figure 2D:
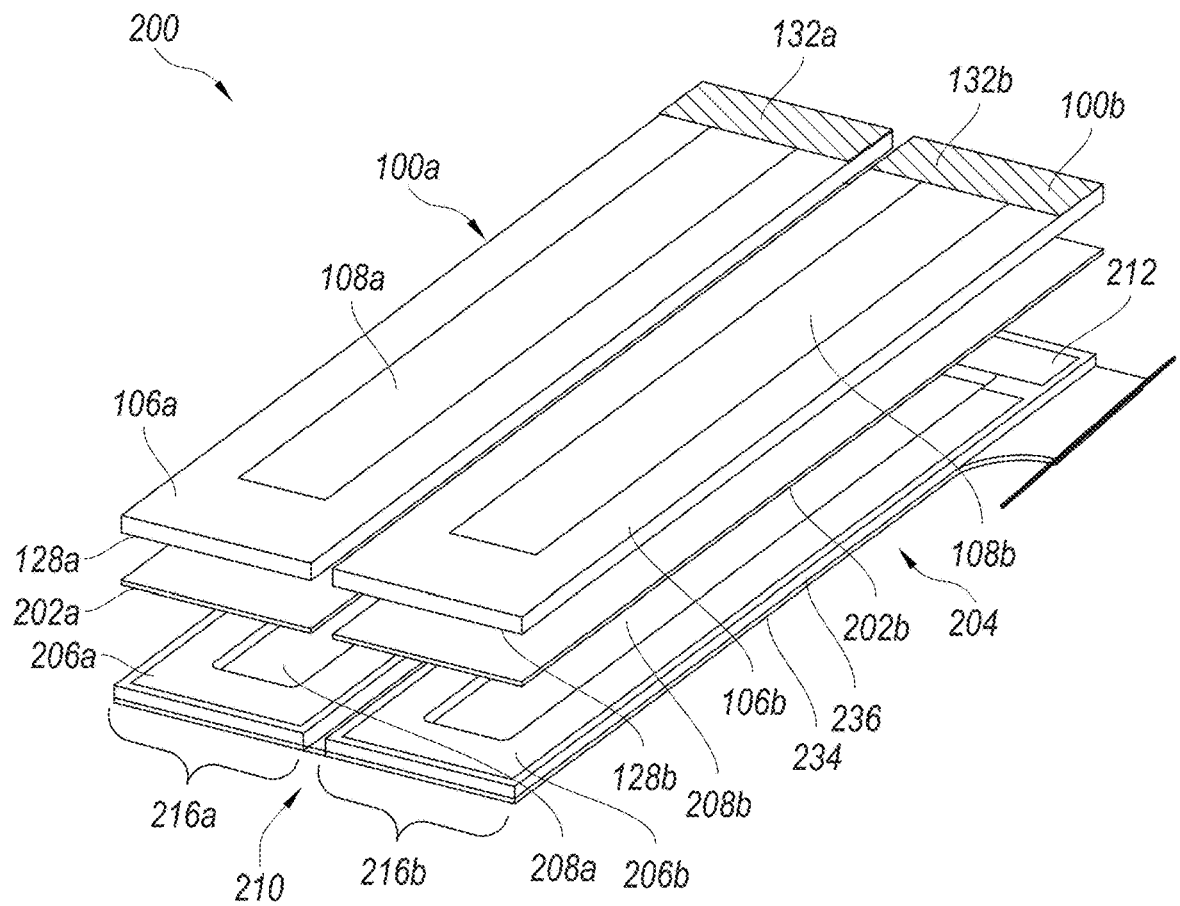
FIG. 2D shows a partially exploded view of the layers of a flexible transducer assembly formed in accordance with embodiments of the present technology.

FIG. 2D shows a partially exploded view of the layers of a flexible transducer assembly 200 formed in accordance with embodiments of the present technology. Two piezo elements 100a, 100b are shown, along with two pieces of z-axis anisotropically conductive tape 202a, 202b and a stiffened flexible (flex) module 204, which may also be referred to as a rigid-flexible (rigid-flex) printed circuit board (PCB) module or a stiffened flex module. When joined together, the flexible transducer assembly 200 forms sealed air gaps 208a, 208b under the active areas 108a, 108b, respectively. One of the piezo elements 100a is configured as a transmitter and one of the piezo elements 100b is configured as a receiver, and both of the elements 100 are aligned to transmit and/or receive ultrasound signals in a direction that is normal to a face of the piezoelectric sheet. In some embodiments, one or both of the piezo elements 100a, 100b can be patterned to both transmit and receive. The stiffened flex module 204 has a hinged area 210 that allows the two elements 100a, 100b to be positioned angularly with respect to each other. This alignment is discussed in further detail below.

Figure 2E:
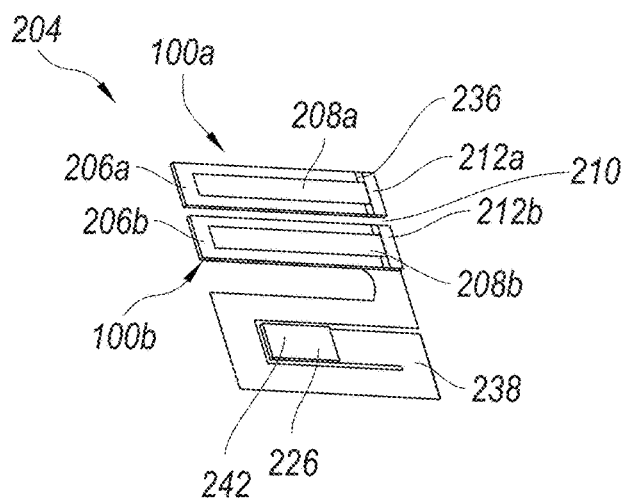
FIG. 2E shows the flexible module used within the flexible transducer assembly of FIG. 2D.

FIG. 2E shows the flex module 204 used within the flexible transducer assembly 200 and will be discussed together with FIG. 2D. The flex module 204 can be made of material such as Polymide and FR4, and includes embedded design circuitry and features that provide appropriate connections and convey signals between the various components and/or layers of the flexible transducer assembly 200 and other circuitry within the patch assembly 10. At least portions of the flex module 204 can have flexibility and stiffness similar to a stiffened flex circuit and/or rigid-flex PCB, and other materials may be used to form the flex module 204 as long as the desired flexibility and stiffness requirements are achieved. The flex module 204 can be fully assembled, for example, at a PCB manufacturing facility and later assembled with the elements 100 and conductive tape 202 to form the flexible transducer assembly 200.

The flex module 204 can include a plurality of layers and thus is not limited by the description of the layers herein. Additionally, one or more of the layers discussed herein can be formed of a plurality of layers. In some embodiments, the flex module 204 can include both a rigid layer 234 (e.g., FR4) and a flex layer 236 (e.g., Polymide). The rigid layer 234 can form two rectangles under the flex layer 236 that are approximately the same size as the elements 100.

The flex layer 236 can be attached to portions of the rigid layer 234 and has portions that extend in the hinged area 210 to join the two rectangles of the rigid layer 234 (discussed in connection with FIG. 2G). The flex layer 236 extends along edge portions of the rectangles that correspond with the borders 106, 132 of the elements 100. The area shown that corresponds to the air gaps 208 is an exposed area of the rigid layer 234 that seals the air backing under the active area 108 and provides mechanical stability to the regions under the elements 100.

The flex layer 236 forms a flexible "tail" 238 that extends away from the elements 100a, 100b. The tail 238 leads to a stiffened tab 226 that can include both the rigid layer 234 and the flex layer 236. A board-to-board connector 242 is shown on the top surface of the stiffened tab 226, although there are other possible connectors that could be used and the position of the connector 242 is not limited as shown. The tab 226 is stiffened to facilitate coupling the connector 242 with other appropriate connections to electronics within the patch transducer 10. The tail 238 is not limited to the shape and configuration shown. In some embodiments, the rigid layer 234 can be included in areas of the tail 238 other than the stiffened tab 226.

The flex module 204 has a first thickness corresponding to the area under the border 106, 132 that is thicker than a second thickness corresponding to the area under the active area 108 of the element 100. Therefore, the flex layer 236 protrudes upward from a flat plane, forming cavities that, when assembled with the elements 100, form the air gaps 208a, 208b.

Electrical contacts are patterned onto a front surface of the flex layer 236. This allows electrical connection to the elements 100 to be achieved with the conductive tape 202a, 202b through the rear surface 128 of the elements 100a, 100b. The electrical contacts can be configured as signal electrodes 206a, 206b and ground electrodes 212a, 212b. In some embodiments, the signal and ground configurations can be swapped.

The signal electrodes 206a, 206b are positioned under the borders 106a, 106b and are not electrically connected to each other (e.g., are isolated from each other) so that the piezo elements 100a, 100b can be driven separately (e.g., one piezo element 100a configured as a transmitter and one piezo element 100b configured as a receiver). The signal electrodes 206a, 206b form a "U-shape" around three sides of the air gap 208a, 208b (two long edges and one short edge) to connect with the rear surface 128 of the elements 100. The electrodes 206a, 206b are connected to covered traces that extend along the length of the flexible tail 238 which leads to the connector 242 on the stiffened tab 226. Trace(s) through the hinged area 210 are also needed to connect the signal electrode 206a to the connector 242 on the stiffened tab 226.

The ground electrodes 212a, 212b are formed on a fourth side of the active area 108a, 108b and positioned to connect with the border areas 132a, 132b on the rear surface 128 of the elements 100a, 100b. The ground electrodes 212a, 212b are electrically separate from the signal electrodes 206a, 206b and can be connected to each other by a trace or ground plane within the flex module 204 through the hinged area 210. The ground electrodes 212a, 212b can be connected to a ground plane that covers most or all of the flexible tail 238 and leads to the connector 242 on the stiffened tab 226. The ground electrodes 212a, 212b on the flex module 204 and ground connections of the elements 100a, 100b can be commonly connected.

Referring again to FIG. 2D, a layer of the z-axis conductive tape 202a, 202b is sandwiched between the rear surfaces 128a, 128b of the elements 100a, 100b and the flex module 204. The conductive tape 202 secures the elements 100 and the flex module 204 together. In some embodiments, the elements 100a, 100b can be aligned with the conductive tape 202a, 202b and flex module 204 by eye or with the use of a jig.

The conductive tape 202 is a z-axis anisotropic conductive tape that conducts between the flex module 204 and the borders of the rear surface 128 on element 100. An example of a z-axis anisotropic conductive tape is 3M® Electrically Conductive Adhesive Transfer Tape 9703, although other z-axis conductive tapes can be used. In other embodiments, other conductive material(s), such as a z-axis conductive film or epoxy embedded with conductive particulates, can be used. An advantage of using the conductive tape 202 is that it eliminates the use of more costly and/or technically difficult manufacturing/assembly processes that require high precision (e.g., thin-film gold deposition, wire bonding, conductive microbead epoxy, soldering, electrical spring clamping processes, etc.) Additionally, because the conductive tape 202 is only conductive in the z-axis direction, the conductive tape 202 does not connect the signal electrodes 206a, 206b to the ground electrodes 212a, 212b. A further advantage of the conductive tape 202 is that it provides conductive electrical contact without heat. In some cases, the 3M® 9703 tape may be used with a minimum overlap area of 5,000 mil2 (3.2 mm2), with a −40° to +85° Celsius (C) temperature range. In some cases, clamping, pressure and/or curing may not be required. In some embodiments, the transducer assembly may be assembled using a minimum initial vertical clamping force of at minimum 5 pounds per square inch (psi) with curing at 75° C. for one hour.

In some embodiments, the conductive tape 202 is sized to provide sufficient surface area for reliable conduction levels between two surfaces for a stated resistance. The inactive border 106, 132 outside the active area 108 provides an increased surface area to bond to the conductive tape 202. In addition to conduction, the larger surface area can be beneficial to allow lower tolerances during assembly. In some cases, if the position of one of the three layers is slightly misaligned during assembly, the surface area can still be sufficient to provide reliable contact and conduction.

For a given gross beam geometry, the active area 108 is largely fixed, although it could be changed to adjust the width, focal depth, etc., of the beam. The border is of a size that provides sufficient area to achieve the necessary conductivity with the conductive tape and forms a non-negligible border around the active element to reduce the side lobes and diffraction. In some embodiments, the border may have a width of approximately 1 mm.

The conductive tape 202 conveys power to the active area 108 through connections in the border 106 and conveys signals between the active area 108 and the flex module 204. Accordingly, the electrodes/elements patterned on the active areas 108a, 108b of the piezo elements 100a, 100b (discussed in connection with FIG. 2A) are electrically connected to conductive traces on/within the flex module 204.

The air gaps 208a, 208b can be formed under most of or the entire acoustically active areas 108a, 108b and are sealed by the conductive tape 202 and the flex module 204. In other embodiments, if the conductive tape 202 does not extend under all or portions of the active areas 108a, 108b, the air gaps 208a, 208b can be sealed between the piezo elements 100 and the flex module 204. The air gaps 208a, 208b provide an acoustic impedance mismatch to prevent/limit the rearward transmission of the ultrasound signals and reflect signals forward to increase transmission power of the patch assembly 10. By backing the entire active areas 108a, 108b with the air gaps 208a, 208b, the maximum amount of energy can be reflected at the air interface. Because the surface area of the element 100 is larger than the active area 108, the electrical connections and sealing of the air gap 208 can be achieved without compromising the air gap 208 under any of the active area 108. This provides an expected advantage compared to an element that has an active area that is the same size of the element, which would require a non-air backing under some of its active area to achieve similar electrical connections and sealing of the remaining air gap 208.

During assembly, the flex module 204 can be provided on a large, flat sheet of rigid-flex material that includes a plurality of the individual flex modules 204. The pieces of conductive tape 202a, 202b and the elements 100a, 100b can be assembled on the flex module 204 in a flat plane using an automated fabrication or manufacturing process, such as "pick and place". To assembly the flexible transducer assembly 200, the conductive tape 202a can connect the piezo element 100a to the portion 216a of the flex module 204, while the conductive tape 202b can connect the piezo element 100b to the portion 216b of the flex module 204. The plurality of individual flex modules 204 can be separated from each other after all of the flex modules 204 on the sheet of rigid-flex material are assembled and tested.

An advantage of the flex module 204 is the ability to mount the piezo elements 100a, 100b on the flat sheet via automated manufacturing without requiring expensive manual assembly, providing a quick and cost-efficient manufacturing process. Other manufacturing methods may be used in other embodiments.

Figure 2F:
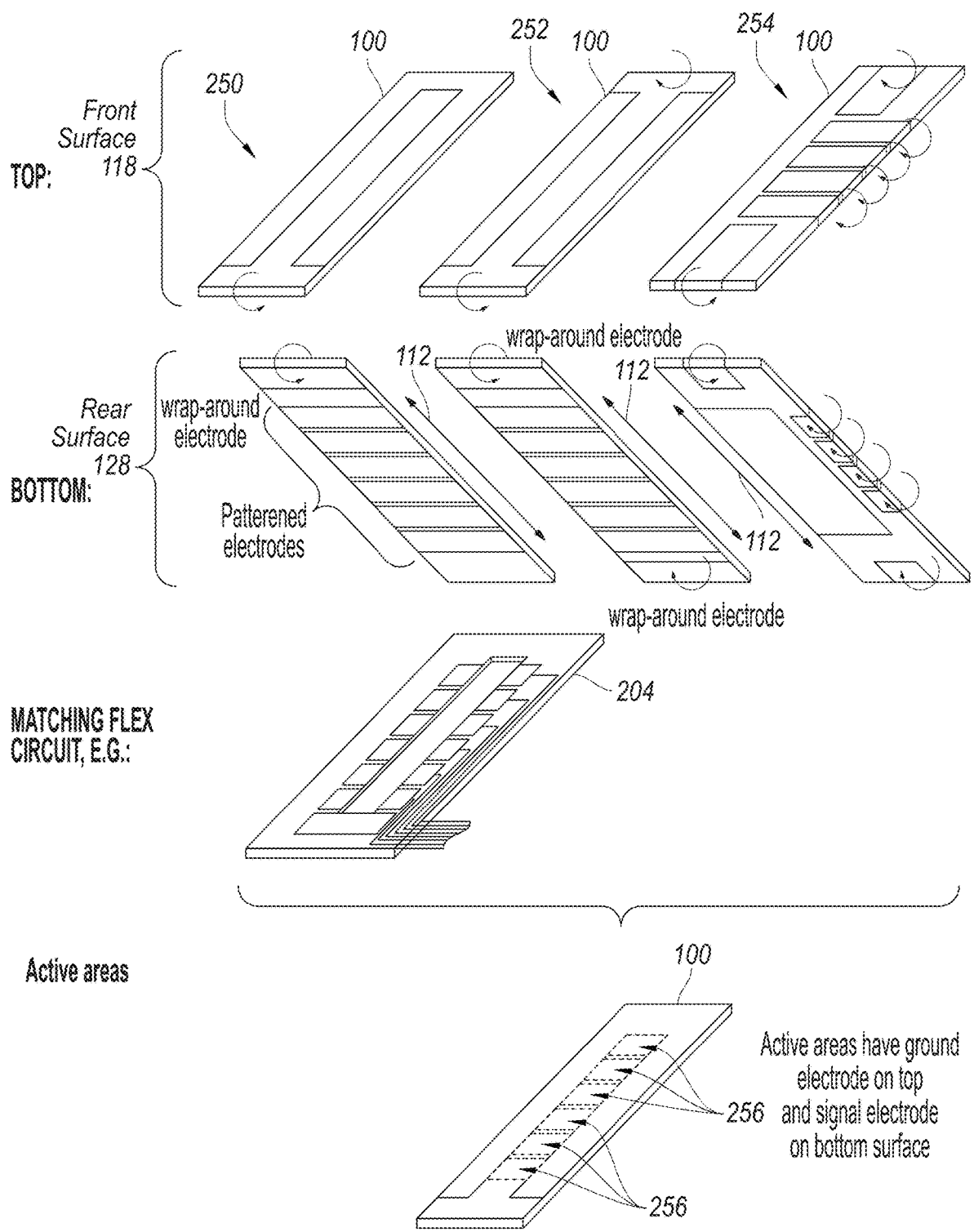
FIG. 2F shows several configurations of patterning an array of elements on the active area of the piezo element of FIG. 2A in accordance with embodiments of the present technology.

In other embodiments, the active area 108 (as shown in FIG. 2A) can be patterned to have more than one element to form an array of elements. FIG. 2F shows several configurations of patterning an array of elements on the active area 108 of the piezo element 100 in accordance with embodiments of the present technology. In the case of multiple transmit/receive elements, element configurations 250 and 252 show different embodiments of patterning the conductive electrode 138 (shown on FIG. 2A) on the rear surface 128 that forms the active area 108. The conductive electrode 138 can be broken into several sections along the long dimension (second dimension 112) to pair with a matching flex module 204 underneath. Corresponding patterning of the front surface 118 is shown. In the example of element configuration 254, the electrode 136 formed on the front surface 118 in the active area 108 can be broken into multiple side-by-side elements, each with a trace connecting them to a wrap-around tab. Active areas 256 are indicated and can correspond with the active areas of the element configurations 250, 252, 254.

Figure 2G:
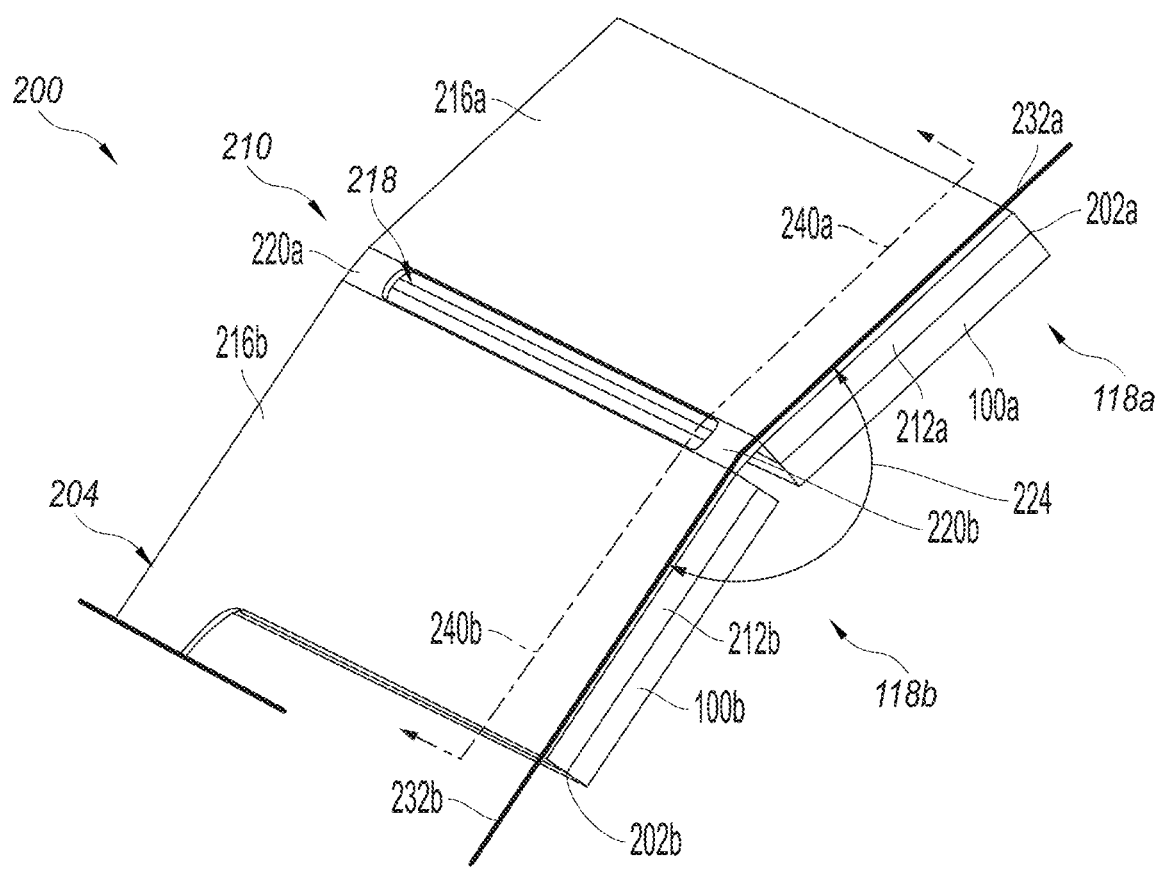
FIG. 2G shows an angled view of the back of the assembled flexible transducer assembly of FIG. 2D.

FIG. 2G shows an angled view of the back and one side of the flex module 204 of the flexible transducer assembly 200. The outside layer of the portions 216a, 216b that is visible in FIG. 2G can be part of the rigid layer 234, as discussed previously in FIG. 2E. In some embodiments, the rigid layer 234 can extend beyond the area under the element 100b toward the tail 238 (indicated in FIG. 2E). Hinge portions 220a, 220b (e.g., part of the flex layer 236) electrically and mechanically connect the portions 216a, 216b of the flex module 204. Therefore, the flexible transducer assembly 200 is "foldable" to adjust the angular orientation between elements 100a and 100b along one of their long sides with respect to each other. This means that flexible transducer assembly 200 with the same construction can be used in multiple configurations that require different angular orientations between the elements 100a and 100b. Although two hinge portions 220a, 220b are shown, in other embodiments a single hinge portion 220 or more than two hinge portions 220 may be used.

The flex module 204 of the illustrated example has at least one opening 218 in the hinged area 210 that can provide mechanical isolation (e.g., break up mechanical waves, such as compression or sheer waves) and a separation of the elements 100a, 100b. In some embodiments, the opening 218 extends approximately the length of the second dimension 112 (FIG. 1) of the active area 108. The mechanical separation improves isolation between the elements 100 and reduces the presence of a possible conduit for acoustic crosstalk between the elements 100. As discussed in more detail below, the opening 218 can also provide a locating feature when assembling the flexible transducer assembly 200 inside a frame, as well as providing a path for air bubbles to escape during the potting process when the flexible transducer assembly 200 is installed in a housing.

The hinged area 210 can provide the flexibility to adjust the angular orientation between the front surfaces 118 of the elements 100a and 100b to improve the ability to target the overlap of the transmit and receive beams for imaging at different depths. As discussed further below, the ability to fix the relative angle of the elements 100a, 100b to achieve different depths of imaging allows the same flexible transducer assembly 200 to be produced in bulk and used for different applications and anatomies. As shown, lines 232a, 232b indicate the planar surfaces of the piezo elements 100a, 100b. The piezo elements 100a, 100b can be physically oriented at a selected angle with respect to each other to allow the ultrasound beams to intersect at a predetermined depth relative to the front surface 118. As used herein, the term depth is generally used to indicate the intersection points of the transmit and receive beams. Angle 224 represents the angular orientation of a plane of the front surface 118a of the piezo element 100a relative to a plane of the front surface 118b of the piezo element 100b. In some embodiments, the angle 224 can be less than 180 degrees, while in other embodiments the angle 224 may be 180 degrees (e.g., the elements 100 are co-planar), while in still other embodiments, the angle 224 may be greater than 180 degrees. At angles of 180 degrees or more, the beams transmitted and received from the elements 100a, 100b may not intersect. In some embodiments, the angle 224 may be between approximately 135 degrees and approximately 180 degrees. The angle 224 is also selected to compensate for the change in beam direction from the Snell's law effect at the transducer/tissue boundary. In some embodiments, one or more lens can be attached to or positioned over the piezo elements 100 to steer the signals transmitted to and received by the piezo elements 100. Examples of lenses are described in U.S. patent application Ser. No. 16/377,028, filed Apr. 5, 2019, (published as U. S. 2020-0022670 A1).

Figure 2H:
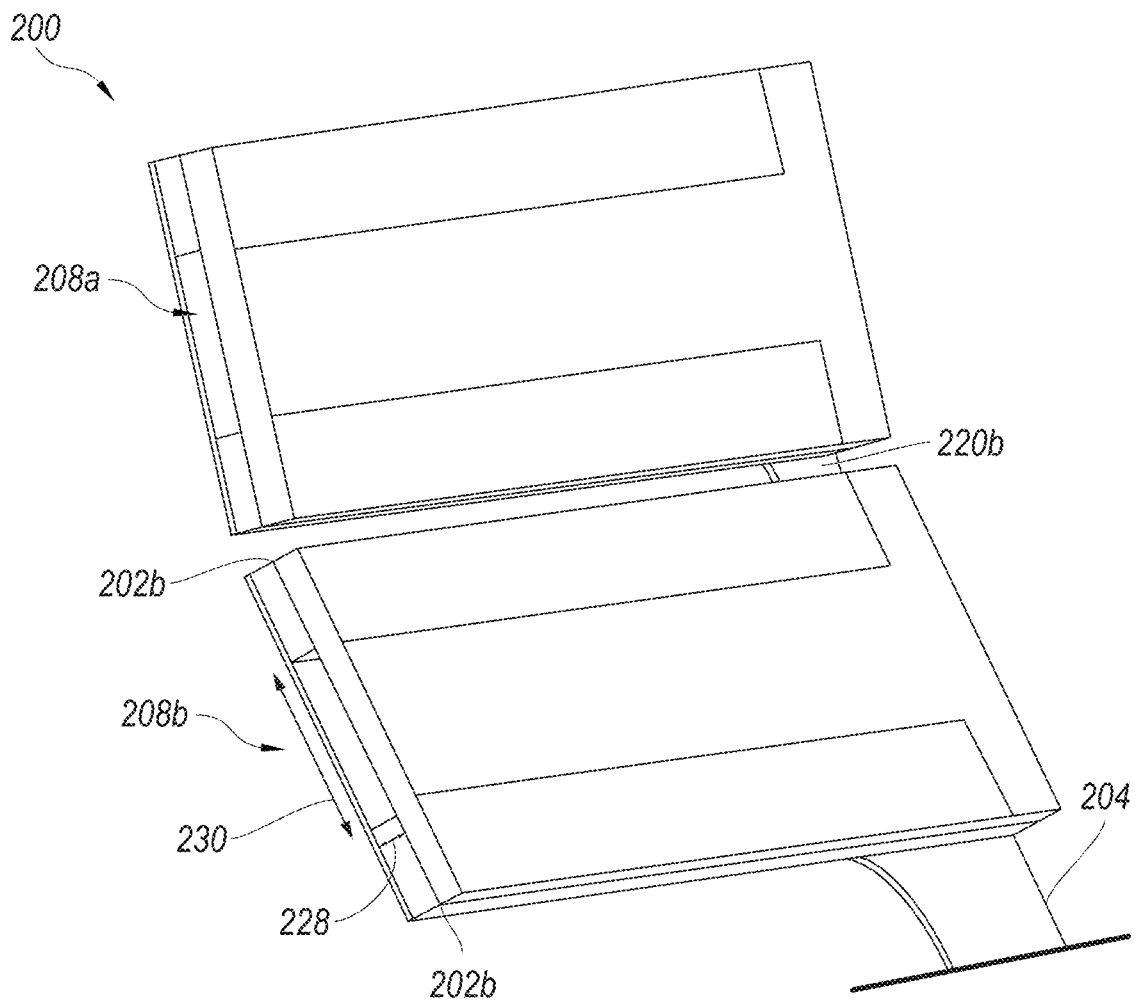
FIG. 2H is a cross-sectional view of the flexible transducer assembly that shows the air gaps beneath the active areas of the piezo elements in accordance with embodiments of the present technology.

FIG. 2H shows a cross-sectional view relative to dotted lines 240a, 240b of FIG. 2G of the flexible transducer assembly 200 with the air gaps 208a, 208b shown. The height 228 of the air gap 208 can generally be defined by the thickness of the conductive tape 202, the flex layer 236 under the border 106, 132, and the electrodes 206, 212. A width 230 of the air gap 208 generally corresponds with the first dimension 110 (FIG. 2A) of the active area 108. Accordingly, the air gap 208 is built into the three-piece flexible transducer assembly 200 (e.g., the flex module 204, the conductive tape 202 and the piezo element 100), and thus is natively formed during the manufacturing/assembly process.

Figure 3A:
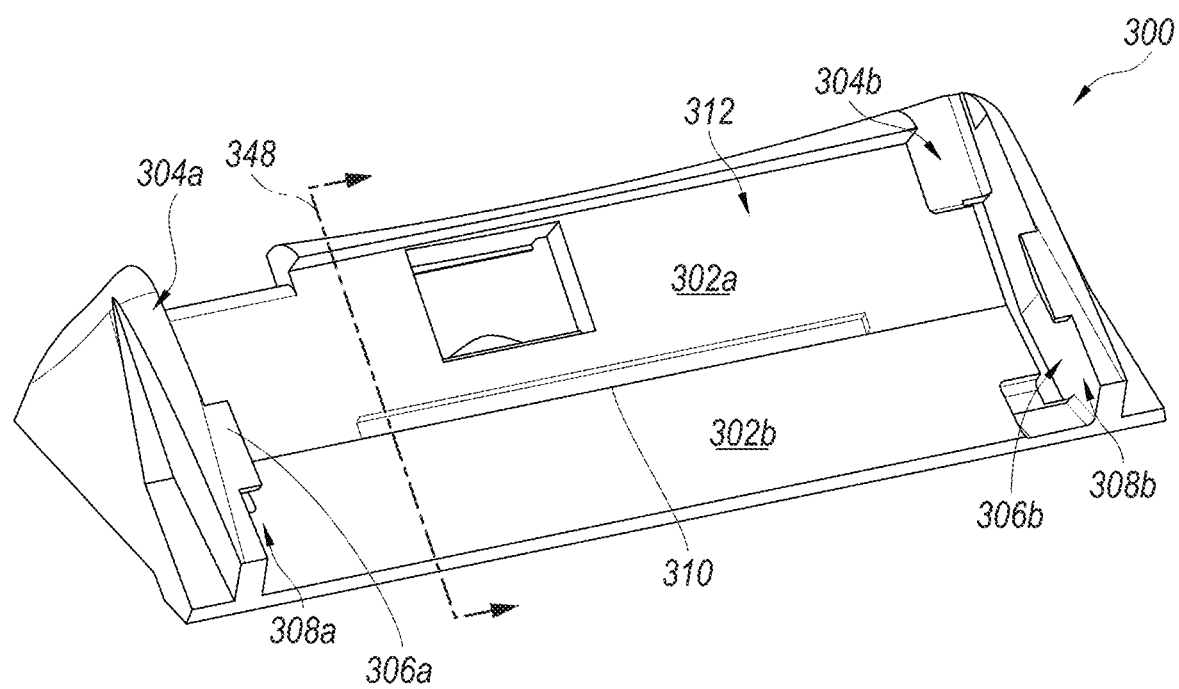
FIG. 3A shows a transducer frame that can support and hold the flexible transducer assembly in a desired angular alignment in accordance with embodiments of the present technology.
Figure 3B:
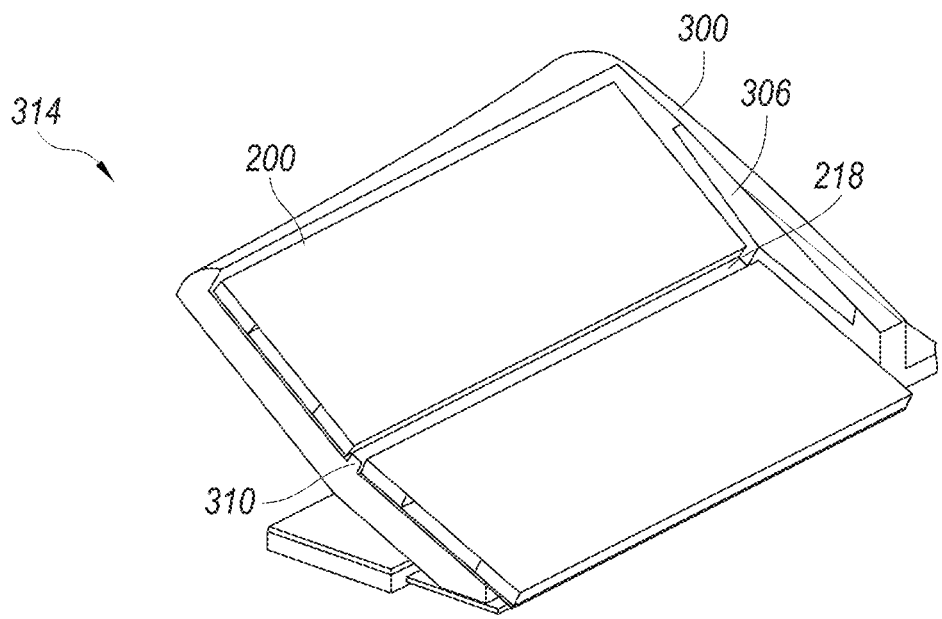
FIG. 3B shows a cross-sectional view of the transducer frame of FIG. 3A with the flexible transducer assembly installed.

FIG. 3A shows an example of a transducer frame 300 that supports and holds the flexible transducer assembly 200 (FIG. 2G) in a desired angular orientation and FIG. 3B shows a cross-sectional view of the transducer frame 300 with the flexible transducer assembly 200 installed (corresponding generally to the dotted line 348 of FIG. 3A). When the flexible transducer assembly 200 is mounted onto the frame 300, the combination forms a frame/transducer unit 314 that can be installed into the housing of the ultrasound patch assembly 10, as discussed in greater detail below. The transducer frame 300 can be made of rigid plastic or other rigid or semi-rigid material that has transducer retention portions configured with a slight give or flex to receive the flexible transducer assembly 200 in a fixed location on the transducer frame 300 so that the elements 100a and 100b are secured at the desired angular orientation relative to each other. The transducer frame 300 can be assembled with the flexible transducer assembly 200 to produce the ultrasound patch assembly 10 quickly, precisely and cost effectively.

Referring to FIG. 3A, the transducer frame 300 of the illustrated example includes first and second bottom surfaces 302a, 302b that are configured to interface with outer surfaces of the portions 216a, 216b (FIG. 2G) of the flex module 204. The first and second bottom surfaces 302a, 302b are each angled to position the elements 100a, 100b at the desired angular arrangement. By altering the angular relationship of the first and second bottom surfaces 302a, 302b relative to each other, the imaging depth of the transducer assembly 200 can be changed. For example, two transducer frames 300 can have substantially identical constructions, except for the angle between the first and second bottom surfaces 302a, 302b. Accordingly, the first and second bottom surfaces 302a, 302b of a first transducer frame 300 may be set in a first angular arrangement to achieve a two centimeter (cm) intersection depth of the ultrasound beams, and the first and second bottom surfaces 302a, 302b of a second transducer frame 300 may be set at a second angular arrangement to achieve a four cm intersection depth. Accordingly, a plurality of different transducer frames 300 may be used to each securely receive a flexible transducer assembly 200 and to securely hold the elements 100a, 100b at the selected but different angular configurations or angles 224 (FIG. 2G) to achieve different imaging depths during use of the ultrasound patch assembly 10, discussed in greater detail below.

Each frame 300 has first and second sidewalls 304a, 304b that extend outwardly from the bottom surfaces 302a, 302b and extend the width of the frame 300 to form a receiving area 312 for the flexible transducer assembly 200. In some cases the sidewalls 304 can extend a portion of the width of the frame 300. One or both of the sidewalls 304a, 304b can include at least one retention feature 306a, 306b that protrudes from the sidewalls 304a, 304b into the receiving area 312 at an outer edge away from the bottom surfaces 302a, 302b. In some embodiments, the retention feature 306a, 306b has a lower surface 308a, 308b configured to interface with the front surface 118 of the flexible transducer assembly 200 after the flexible transducer assembly 200 has been pressed past one or both of the retention features 306a, 306b to securely capture the flexible transducer assembly 200 in place and prevent the flexible transducer assembly 200 from moving away from the bottom surfaces 302a, 302b.

An alignment rib 310 extends outwardly into the receiving area 312 at the vertex of the first and second bottom surfaces 302a, 302b. Although a single alignment rib 310 is shown, more than one alignment rib 310 may be formed. The alignment rib 310 can extend the width or nearly the width of the opening 218, within tolerances. FIG. 3B shows the alignment rib 310 extending into the opening 218 of the flex module 204 of the flexible transducer assembly 200. In some embodiments, the alignment rib 310 provides an alignment surface against which the flexible transducer assembly 200 is positioned to register and ensure that the flexible transducer assembly 200 is in the correct and precise location relative to the frame 300. In some embodiments, the alignment rib 310 can interface with the rigid layer 234 and at least a portion of the flex layer 236. Accordingly, all of the frames 300 have the alignment rib 310 in the same location even though the angular orientation of the bottom surfaces 302a, 302b may be different in different frames 300.

Although the alignment rib 310 of the illustrated example provides a surface against which the flexible transducer assembly 200 is registered during assembly, other embodiments can use one or more other registration surfaces and/or features to quickly, easily and accurately align the flexible transducer assembly 200 with the frame 300. For example, the frame 300 can include one or more different protrusions that interface with one or more alignment features of the flex module 204. In other embodiments, the flex module 204 can include protruding alignment feature(s) that interface with corresponding alignment feature(s) of the frame 300.

In other embodiments, the alignment rib 310 may not touch or interface with either of the elements 100a, 100b to prevent the transmission of waves between the two transducers. Therefore, the hinge portions 220a, 220b (FIG. 2G) can be sized to prevent all or some of the alignment rib 310 from touching the flexible transducer assembly 200.

In some embodiments, during assembly the flexible transducer assembly 200 may be tilted and placed under one of the retention features 306 on one end of the frame 300, aligned to allow the alignment rib 310 to extend into the opening 218, and then pressed into the frame 300, causing one or both of the sidewalls 304 to flex outwardly until the other end of the flexible transducer assembly 200 is under the second retention feature 306. The combination of the flexible transducer assembly 200 and the frame 300 forms the frame/transducer unit 314 that can be installed into the housing of the ultrasound patch assembly 10, as discussed in greater detail below. A person of ordinary skill in the art can appreciate that other physical arrangements, such as protrusions of various shapes and sizes, recesses, slots, etc. can be provided in the frame 300 or on the flexible transducer assembly 200 to receive and securely hold the flexible transducer assembly 200 in a fixed position on the frame 300.

Figure 3C:
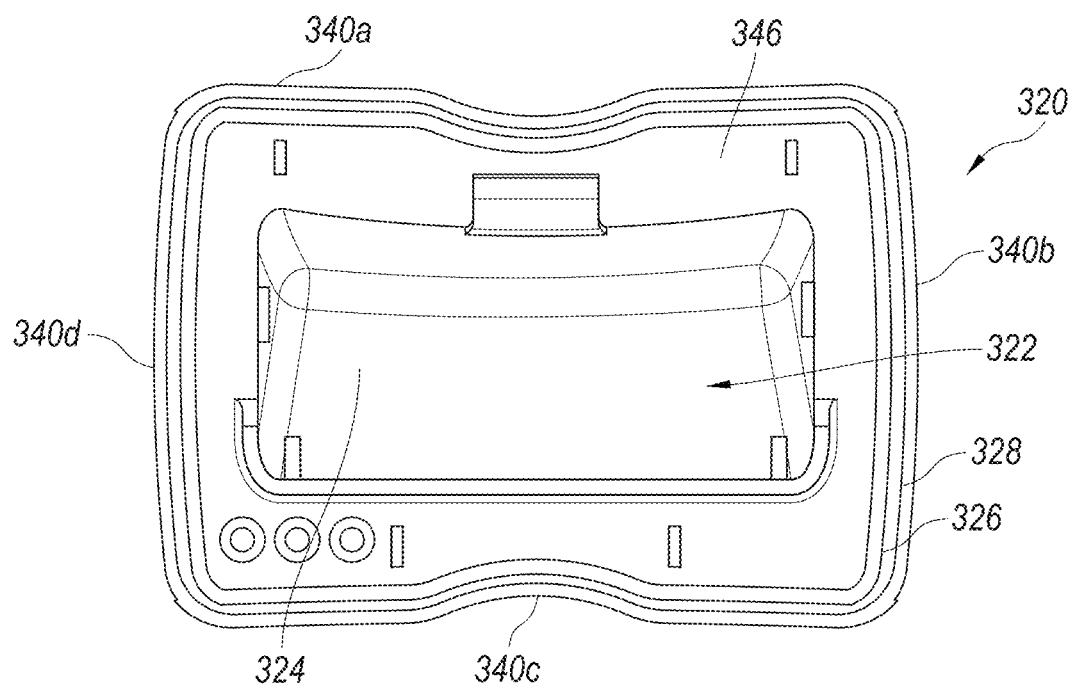
FIG. 3C shows an interior area of a base of the ultrasound patch assembly formed in accordance with embodiments of the present technology.

FIG. 3C shows an interior area of a base 320 of the ultrasound patch assembly 10 formed in accordance with embodiments of the present technology. The base 320 has a bottom surface 346 that has a central portion that protrudes outwardly to form a cavity 322. The cavity 322 is configured to receive and retain the assembly of the frame/transducer unit 314 (FIG. 3B) within the base 320. When the frame/transducer unit 314 is positioned in the base 320, the elements 100 of the flexible transducer assembly 200 are positioned near or closely proximate to an inner surface of the cavity 322. An outer surface (not shown) forms a wedge face 324 that is configured to interface with the patient. As the elements 100 are very close to the inner surface of the wedge face 324 and thus also the target area of the patient, lower power is needed compared to an arrangement where ultrasound elements are positioned further from the target area of the patient.

The base 320 has sidewalls 340 (individually identified as 340a, 340b, 340c and 340d) that protrude upwardly from the bottom surface 346 of the base 320. The upper edges 326 of the sidewalls 340 can have one or more protrusion 328, recess and/or other interlocking members to facilitate mating the base 320 and a top shell (shown below in FIGS. 4A-4C) of the ultrasound patch assembly 10.

Figure 3D:
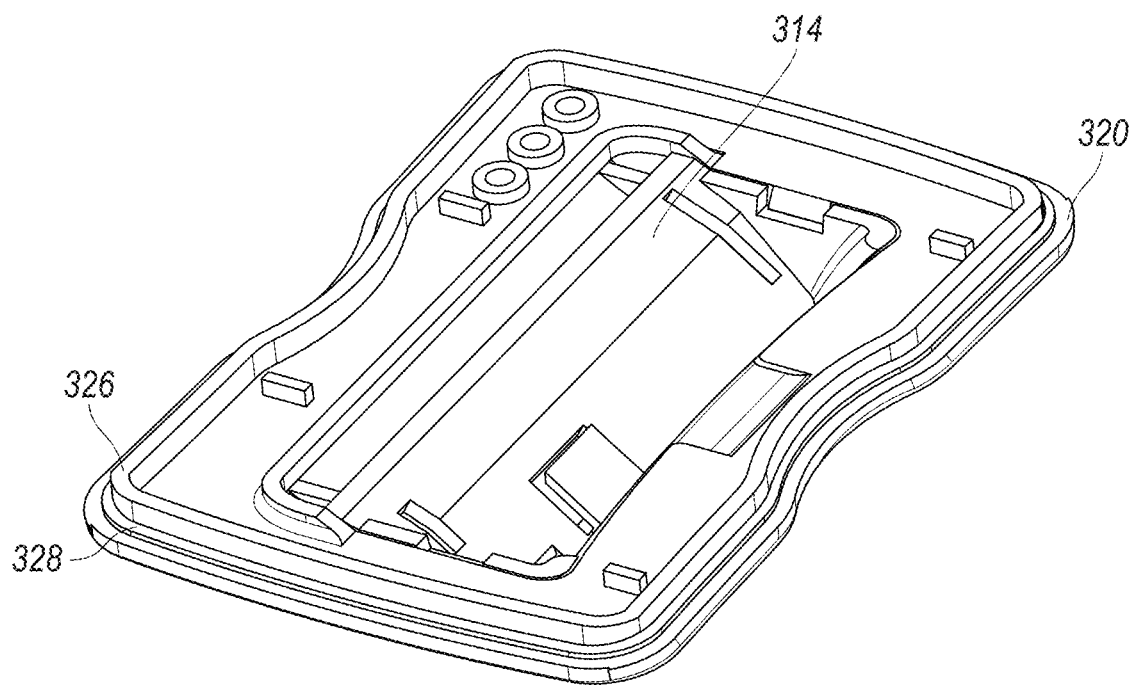
FIGS. 3D and 3E show views of the base of FIG. 3C mated with the transducer frame and flexible transducer assembly in accordance with embodiments of the present technology.
Figure 3E:
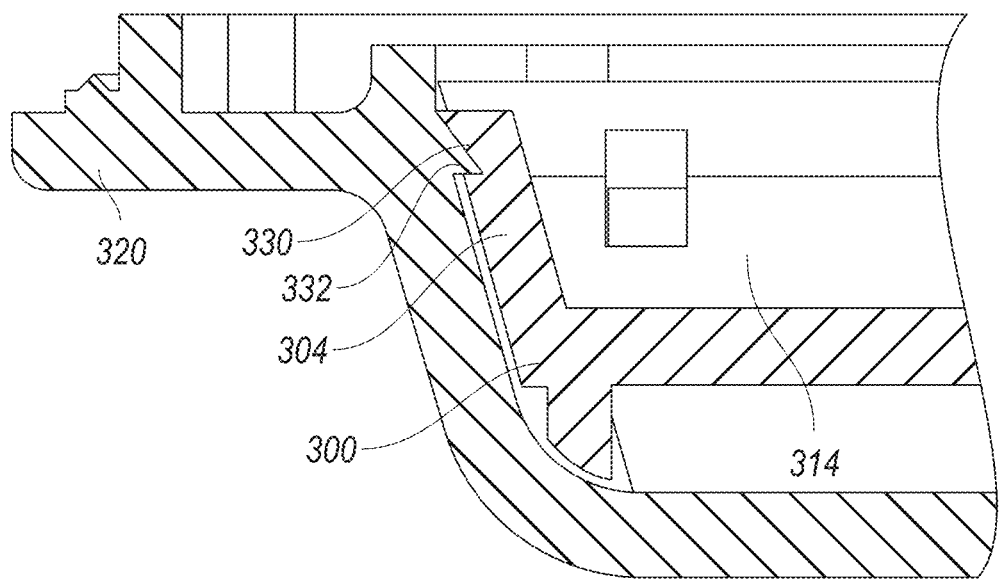

FIGS. 3D and 3E show views of the base 320 mated with the frame/transducer unit 314 in accordance with embodiments of the present technology. In some embodiments the transducer frame 300 and/or frame/transducer unit 314 can be fully held within the cavity 322, while in other embodiments, the transducer frame 300 and/or frame/transducer unit 314 can be partially held within the cavity 322. In still other embodiments, such as when the bottom surface 346 of the base 320 is flat, the transducer frame 300 and/or frame/transducer unit 314 can be held or positioned proximate the bottom surface 346. The manufacturing tolerances for the distance and angles in the support and alignment members of the base 320 and the frame 300 are strictly controlled to provide the precision needed to achieve the directionality of the piezo elements 100. Furthermore, each transducer frame 300, regardless of the angular orientation of the elements 100a, 100b, is configured to mate with the same base 320, providing the ability to manufacture the ultrasound patch assemblies 10 that can be used in different scanning applications while using the same manufacturing processes, the same base 320, and the same flexible transducer assembly 200.

Accordingly, the base 320 is configured with a common frame footprint that quickly, easily and accurately accepts any one of the plurality of frames 300 that support the piezo elements 100 of the respective flexible transducer assembly 200 at the selected angular orientations relative to each other. This simple and precise process facilitates quick assembly and can eliminate the need for costly trained labor.

FIG. 3E shows a retention member 330 that extends from an inner surface of the base 320. A bottom edge 332 of the retention member 330 engages a top surface of the sidewall 304 of the frame 300 (e.g., sidewall 304a shown in FIG. 3A) to hold the frame 300, and thus the frame/transducer unit 314, in a fixed position within the base 320. Although only one side is shown in FIG. 3E, an opposite side of the base 320 can also have a retention member that interfaces with the top surface of the other sidewall 304b. During assembly, the frame/transducer unit 314 can be pressed into the base 320 so the retention member 330 holds the frame 300 in place and secures the components in a fixed arrangement relative to each other. In some embodiments, the base 320 may be configured to elastically flex outwardly to receive the frame 300 during assembly, and the base 320 returns to its unflexed position once the frame/transducer unit 314 is pressed into position. Although not shown, it should be understood that other retention member(s) may be provided, such as protrusions from the inner surface of the cavity 322 and base 320 that mate with openings in the frame 300 and vice versa.

The relationship between the center distance or vertex of the elements 100a, 100b, the angle 224 (FIG. 2G) of the elements 100a, 100b relative to each other, the acoustic medium between the elements 100a, 100b and the inner surface of the wedge face 324, as well as the thickness of the material of the wedge face 324 have specifically defined and controlled tolerances. For example, the thickness of the material of the wedge face 324 can be within a range of about 0.5 mm to 2 mm, although other thicknesses can be used.

To ensure quality imaging, a suitable acoustic medium, such as epoxy, is used to encapsulate and permanently fix the frame/transducer unit 314 in the base 320, so as to provide sonic continuity between the piezo elements 100 and the inner surface of the wedge face 324. This process may generally be referred to as potting. In some embodiments, a portion of the cavity 322 of the base 320 can be filled with epoxy prior to installing/snapping the frame/transducer unit 314 into the base 320. The epoxy may be allowed to level before carefully inserting the frame/transducer unit 314. Air bubbles that may become trapped between the front surfaces 118 of the piezo elements 100 can escape through the opening 218 in the hinged area 210 or other holes in the frame 300. In some embodiments, one or more holes can be provided in the frame 300 to provide additional path(s) for the bubbles to escape.

Figure 3F:
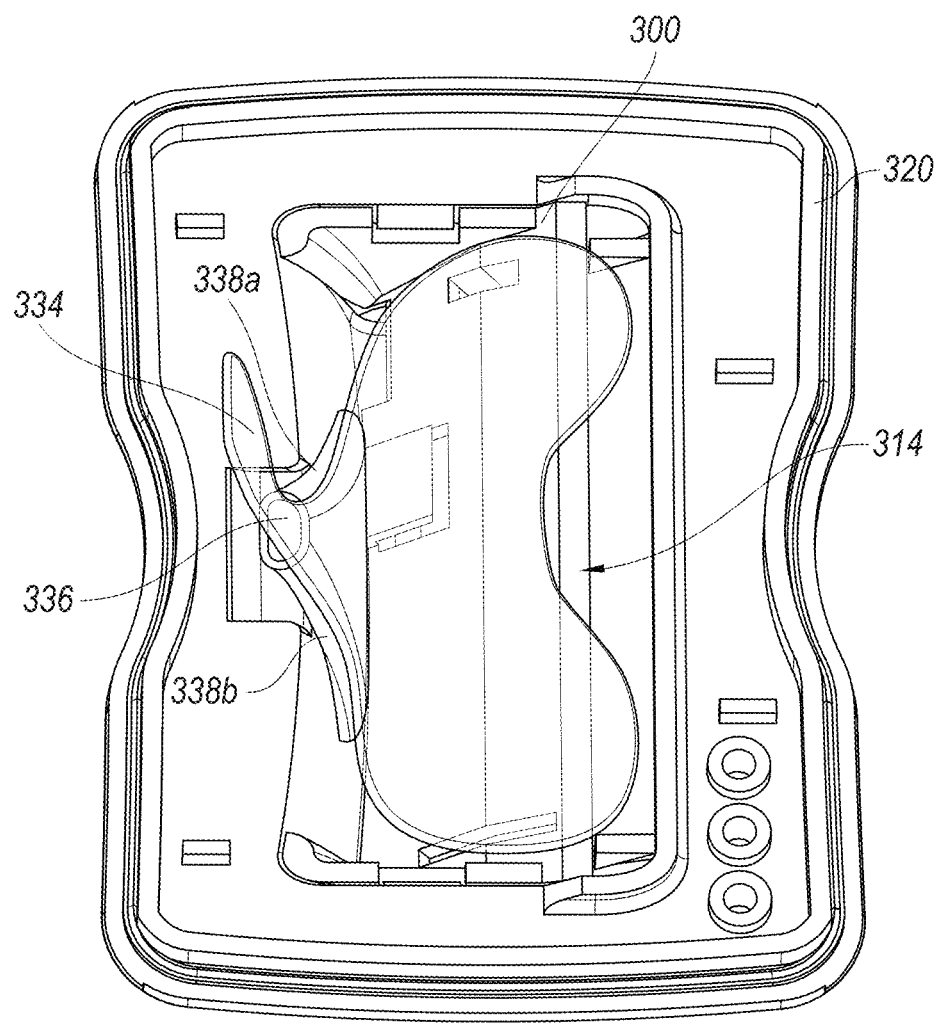
FIG. 3F shows an example of geometry guided epoxy potting of the ultrasound patch assembly in accordance with embodiments of the present technology.

FIG. 3F shows an example of geometry guided epoxy potting of the ultrasound patch assembly 10 in accordance with embodiments of the present technology. A guide hole 336 and one or more potting channels 338a, 338b are provided adjacent to the area in the cavity 322 that receives the frame/transducer unit 314. The guide hole 336 and channels 338a, 338b can be molded into the portion of the base 320 that forms the cavity 322.

Referring also to FIG. 3C, after the frame/transducer unit 314 has been snapped into the base 320, the epoxy 334 can be deposited or provided (e.g., such as through a nozzle of a syringe, a deposition gun, etc.) through the guide hole 336 or directly into one or more of the potting channels 338a, 338b that funnel the epoxy 334 to the area between the piezo elements 100 and the inside surface of the base 320 along the wedge face 324. The epoxy 334 or other potting material, shown in shadow on FIG. 3F, can be introduced into the channels 338a, 338b, and the channels 338a, 338b direct the flow of epoxy into the cavity 322 to encapsulate the frame/transducer unit 314 affixed within the base 320. The epoxy 334 can be selected based on its acoustic properties, such as speed of sound and attenuation, to ensure that the angle of the beam as it exits/enters the base 320 is known and does not change.

In some embodiments, the epoxy 334 can be provided through the guide hole 336 and flows through the channels 338a, 338b to feed opposite ends of the elements 100. In other embodiments, an additional channel (not shown) can be provided to feed the center area under the piezo elements 100. The controlled manner in which the epoxy 334 is applied can flood the inside of the base 320 uniformly and cover at least the front surfaces 118a, 118b of the piezo elements 100a, 100b of the flexible transducer assembly 200. The controlled application of epoxy 334 can also allow for air bubbles to rise and escape from the assembly. In some cases, this method can be done at atmosphere, making sure that the syringe or deposition gun is free of air so that bubbles are not introduced into the epoxy 334.

This potting process can allow for a fast, repeatable, machine compatible application of potting material. An advantage of this configuration and method is that quality is controlled from batch to batch and can provide for increased speed in manufacturing.

Figure 4A:
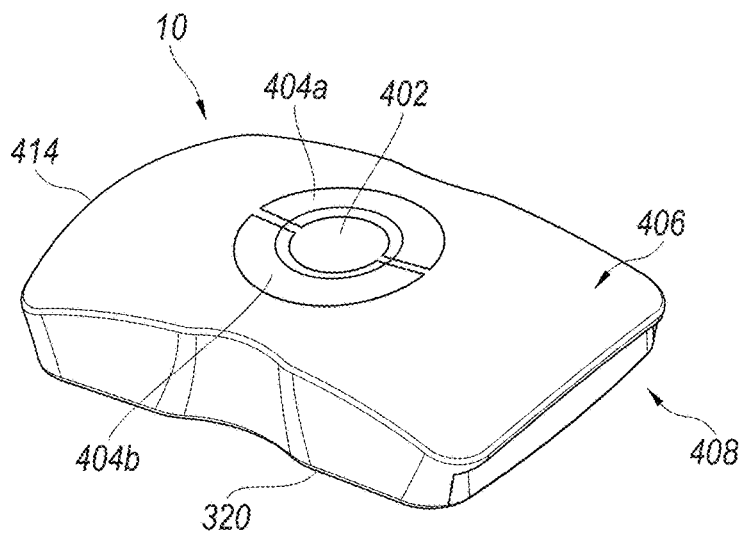
FIG. 4A shows a view of the top of the ultrasound patch assembly that includes the flexible transducer assembly and the frame therein in accordance with embodiments of the present technology.

FIG. 4A shows an assembled ultrasound patch assembly 10 that includes the flexible transducer assembly 200 and the frame 300 therein in accordance with embodiments of the present technology. The housing of the patch assembly 10 includes top shell 414 and the base 320 that can be configured to be snapped together. A bottom side 408 of the patch assembly 10 is configured to interface with the skin of a patient (e.g. skin contacting portion 14 of FIG. 1). A button 402 on a top side 406 can provide the ability to turn the patch assembly 10 on and off. One or more lights 404a, 404b can indicate the powered status of the patch assembly 10, can flash to indicate wireless pairing with a remote device, and can glow a different color or provide a different indication (e.g., flash sequence) to indicate when the battery is low, etc.

Figure 4B:
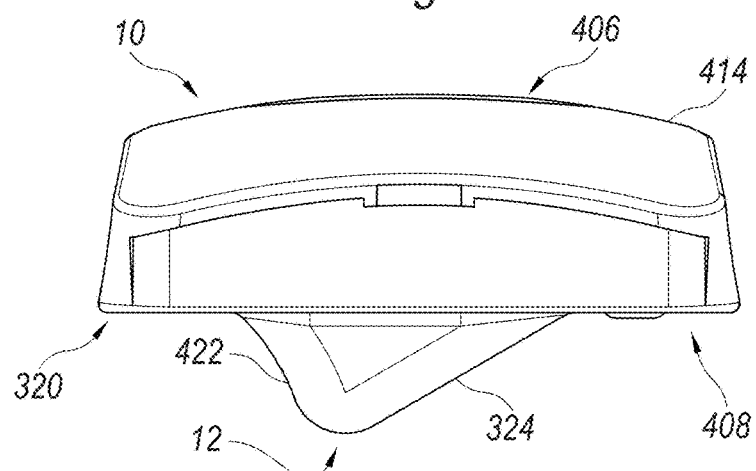
FIGS. 4B and 4C show side and angled bottom views, respectively, of the ultrasound patch assembly of FIGS. 1 and 4A.

FIG. 4B shows a side view of the ultrasound patch assembly 10 of FIGS. 1 and 4A. The wedge 12 protrudes from the bottom side 408. Referring also to FIGS. 3B and 3C, the frame 300 with the flexible transducer assembly 200 is positioned within the cavity 322 of the wedge 12 of the patch assembly 10 such that the piezo elements 100 transmit and receive signals through the wedge face 324. The wedge 12 includes a back side 422 that is smaller than the wedge face 324. Therefore, a user of the patch assembly 10 can easily tell which side of the wedge 12 transmits/receives ultrasound.

The two-piece shell of the ultrasound patch assembly 10 can be formed of a plastic or elastomeric material (e.g., silicone, powder-loaded silicone, etc.) that provides a relatively good acoustic match to the tissue to be examined. At a minimum, the material that is used at least for the wedge 12 should not excessively attenuate or reflect the transmitted or reflected (e.g., detected or received) ultrasound energy. In some embodiments, the top shell 414 can be formed of a different material than all or portions of the base 320.

It is easier to detect fluid flow in a vessel by measuring a Doppler shift in ultrasound signals that are transmitted and received at an angle to the fluid flow being measured. If the piezo elements 100, which transmit and receive normal to the piezo material, are placed directly on, or parallel to, a subject's anatomy, the ultrasound signals will be primarily transmitted and received in a direction that is nearly orthogonal to the fluid flow in the vessel.

By installing the flexible transducer assembly 200 in the wedge 12 or other protrusion, the signals can be steered or directed in a direction that is not orthogonal to the fluid flow. When scanning a patient, the ultrasound signals are transmitted and received through the wedge face 324 that is coupled to the subject's skin with an acoustic coupling medium, such as acoustic gel. The wedge face 324 holds the piezo elements 100 at an angle with respect to a direction normal to the skin surface or the bottom side 408 of the ultrasound patch assembly 10. In some embodiments, the wedge 12 is sized to fit in a notch in a subject's neck near the carotid artery and jugular vein.

In some embodiments, the wedge 12 is shaped to set a transmit/receive direction in a range from about 20-60 degrees with respect to the direction of flow in a vessel. In some cases, the preferred angle is approximately 30 degrees. The focus area for the piezo elements 100 can overlap in an area of interest at a desired depth determined, at least in part, by the angle 224 (FIG. 2H).

Figure 4C:
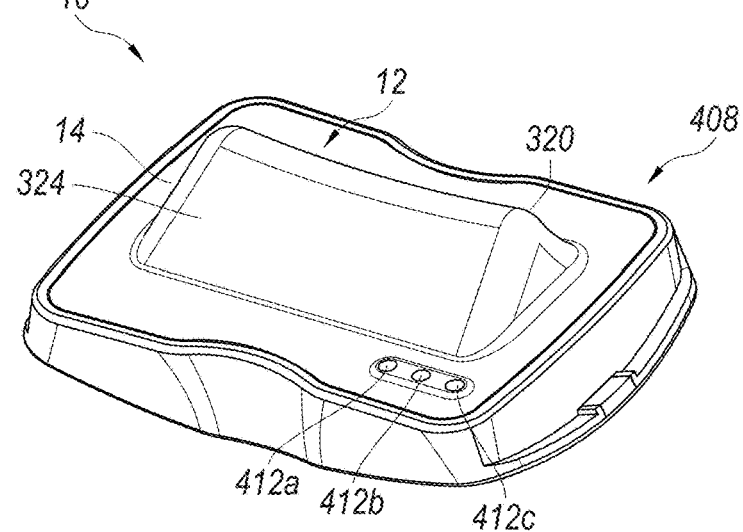

FIG. 4C shows an angled bottom view of the ultrasound patch assembly 10 of FIGS. 1 and 4A. The wedge 12 and associated outer surface of the wedge face 324, as well as the skin contacting portion 14, are indicated on the patch assembly 10. In other embodiments, the base 320 can have a protrusion of a different shape and/or size than shown. In still further embodiments, the bottom side 408 may form a substantially flat surface.

One or more contacts 412a, 412b and 412c are shown on the bottom side 408 of the base 320. In some embodiments, the contacts 412 can be used for charging/recharging the ultrasound patch assembly 10, collecting data when the ultrasound patch assembly 10 is not interfacing with a patient, and logging the patch assembly 10 (e.g., identifying patient use, time of procedure, sterilization performed, etc.).

In some embodiments, an adhesive can be used to attach at least part of the skin contacting portion 14 to the skin of a patient, while an acoustic coupling material is used between the skin of the patient and the outer surface of the wedge face 324. Adhesives and acoustic coupling materials, either as separate materials or a combined material are disclosed in U.S. Patent Application Publication No. 2017/0332995, filed Jun. 9, 2017, and which is incorporated herein by reference in its entirety.

A fastener or adhesive can be used over at least a portion of the top side 406 of the patch transducer 10 to further secure it to the patient. This can provide the advantage of preventing undesirable decoupling, movement, or migration of the patch transducer 10 away from the desired imaging location. In some cases, the patch transducer 10 can move or migrate on the patient over time or when the patient moves or is moved, and thus may image a different location of the patient or become decoupled from the patient. An adhesive can be made of tape or bandage materials, or can be a film dressing such as Tegaderm®, which is produced by 3M®. An adhesive can provide a force normal to the skin of the patient to retain the patch transducer 10 in a fixed position relative to the patient's skin. Some adhesives can provide a compressive force to hold the patch transducer 10 in the fixed position, thus retaining the patch transducer 10 in proper alignment (e.g., vertical, angular, lateral, etc.). In some cases, some adhesives can interface with the skin of the patient and provide a pulling force that securely pulls the skin proximate the patch transducer 10 toward the patch transducer 10. Other fastening mechanisms such as a strap may be used, such as those disclosed in U.S. patent application Ser. No. 16/377,028, filed Apr. 5, 2019, (published as U. S. 2020-0022670 A1).

In some cases, a hydrophobic or foam adhesive ring (not shown) can be used attached to the skin contacting portion 14. The hydrophobic adhesive ring can provide a barrier to prevent the seepage of acoustic coupling beyond the outer edges of the patch transducer 10. The hydrophobic adhesive ring can also attach the patch transducer 10 to the patient, or can be used together with another fastener/adhesive. In other embodiments, a well or depression (not shown) can be formed in the skin contacting portion 14 between the wedge 12 and outer edges of the patch transducer 10 and/or adhesive/fastener that interfaces with the skin contacting portion 14 to collect acoustic coupling medium that may seep beyond the outer surface of the wedge face 324.

Although the patch transducer 10 is shown with the wedge 12 extending outward from the bottom surface, in some embodiments the patch transducer 10 may have a substantially flat bottom side 408 that interfaces with the patient. In this case, the transducer frame 300 holds the piezo elements 100 at the desired angular arrangement and is fully within the housing. In some embodiments, the patient interfacing surface of such a patch transducer 10 may have a height comparable to that between the top side 406 and a bottom edge of the wedge 12. One or more lens can be used to steer the ultrasound signals.

Figure 4D:
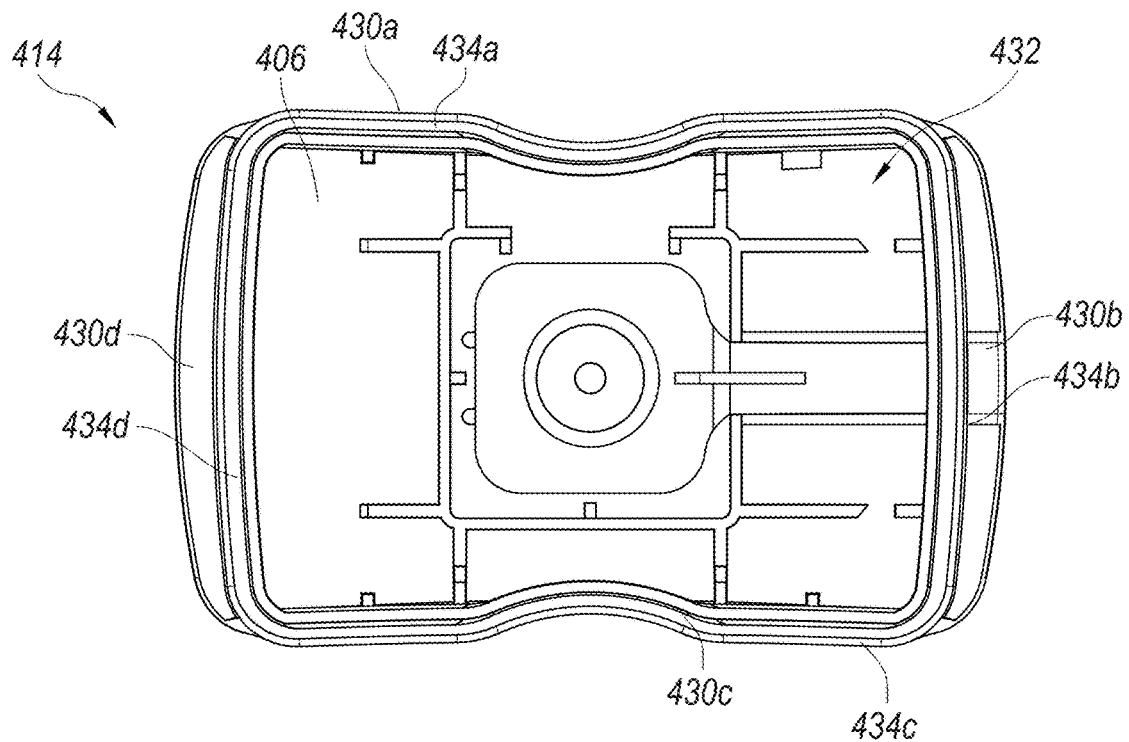
FIG. 4D shows a view of the inside of a top shell of the ultrasound patch assembly in accordance with embodiments of the present technology.

FIG. 4D shows a view of the inside of a top shell 414 of the ultrasound patch assembly 10 in accordance with embodiments of the present technology. Sidewalls 430 (indicated individually as 430a, 430b, 430c and 430d) protrude upwardly from around outer edges of the top side 406 to form a cavity 432. Top edges 434 (identified individually as 434a, 434b, 434c, and 434d) of the sidewalls 430 can include one or more protrusions, recesses, and/or other interlocking members that are configured to mate with the base 320.

Figure 4E:
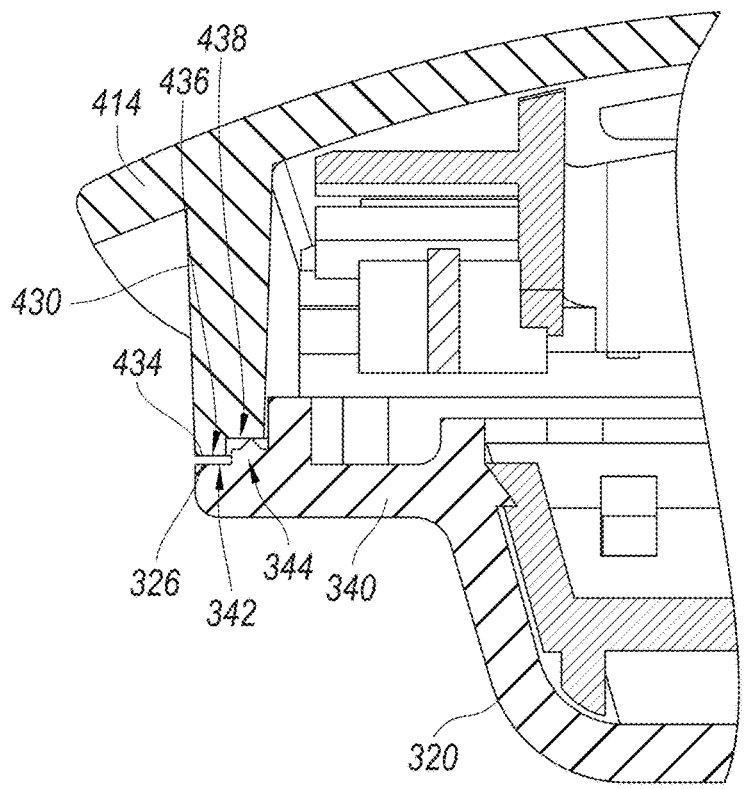
FIG. 4E shows example interfacing elements of the top shell and base of the ultrasound patch assembly when mated together in accordance with embodiments of the present technology.

FIG. 4E shows example interfacing elements of the top shell 414 and base 320 when mated together in accordance with embodiments of the present technology. For example, the top shell 414 and base 320 may be snapped together.

In some embodiments, the top edge 434 of the sidewall 430 of the top shell 414 has a first portion 436 that extends further toward the base 320 than a second portion 438. The first and second portions 436, 438 can be substantially flat. The top edge 326 of the sidewall 340 of the base 320 includes a first portion 342 that is slightly longer than the first portion 436 of the top shell 414. The first portion 342 can be substantially flat. A second portion 344 extends further toward the top shell 414 than the first portion 342 and can include an ultrasonic weld line. The ultrasonic weld line can create a hermetic seal and allow the ultrasound patch assembly 10 to be submersible in cleaning agents, as well as preventing tampering with the patch assembly 10.

An advantage of the two-part shell construction is that the ultrasound patch assembly 10 can be fully assembled inside the base 320. In other embodiments, some of the components can be fixed inside the top shell 414 before the top shell 414 and base 320 are mated together. This facilitates a systematic and reproducible manufacturing process. Other components, interconnects and structure designed to provide the desired functionality and secure the components (e.g., circuit board(s), battery, electronics, memories, antenna, speaker, etc.) that generate the ultrasound signals, detect a Doppler shift in a vessel and produce an output indicative of the Doppler shift as well as transmit the signal data to a remote device can be held within the top shell 414 and/or base 320. The remote device or base unit (e.g., dedicated ultrasound machine, computer and/or handheld device such as a smart phone or tablet that has an application installed thereon for communicating with the patch assembly 10) can transmit and receive information to/from the patch assembly 10.

In some embodiments, the patch assembly 10 can be used by a single patient. In other embodiments, the patch assembly 10 can be refurbish-able (e.g., facilitate an upgrade, repair, etc.) and/or repurposed for use with multiple patients. Accordingly, the waterproofing can allow for the sterilization of the patch assembly 10 when using hydrogen peroxide or other appropriate cleaning chemicals, and/or ultrasonically cleaning in a liquid solution.

The flexible transducer assembly 200 discussed above includes two separate, wide piezo elements 100, often having one piezo element 100a configured to transmit and one piezo element 100b configured to receive. When used in the ultrasound patch assembly 10, this configuration can simplify the placement of the piezo elements 100 over the vessel of interest. Therefore, a lower skilled technician or a medical employee without significant ultrasound scanning training and/or experience can place the ultrasound patch assembly 10 on the patient with a high degree of success.

Figure 5A:
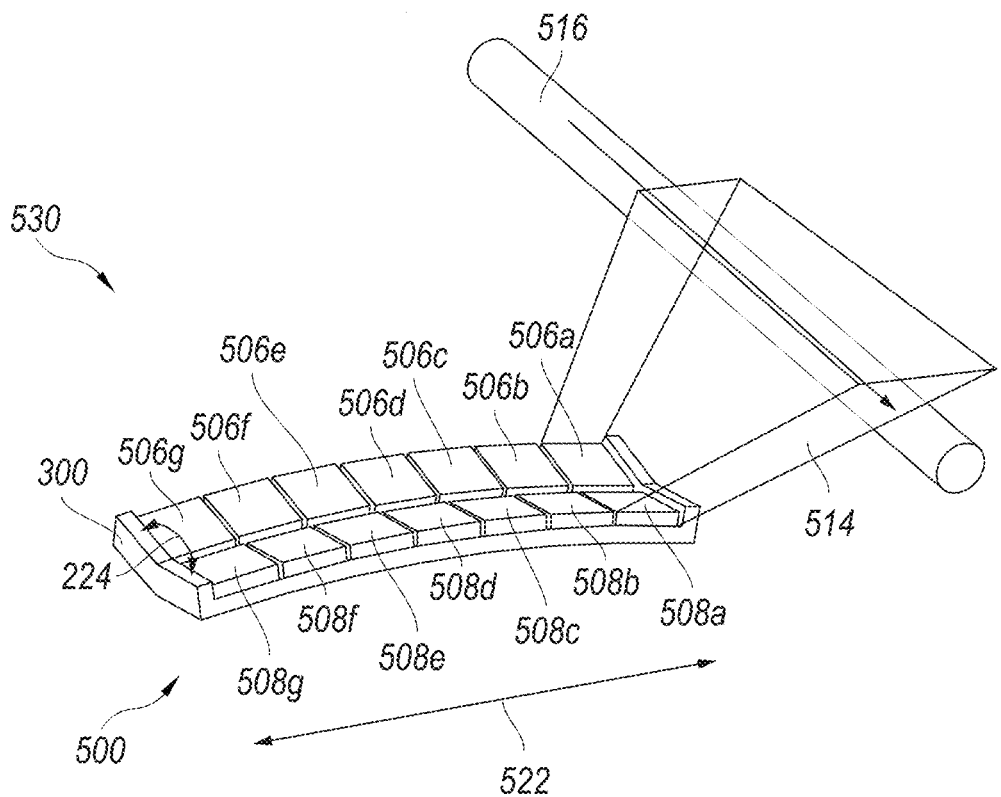
FIG. 5A shows another example of a flexible transducer assembly that includes an array of separate transducer piezo elements in accordance with embodiments of the present technology.

In some cases, the use of the wide piezo elements 100 can result in some of the received ultrasound energy (e.g., detected echo signals) arising from stationary tissue, which acts as noise compared with the desired Doppler signal. FIG. 5A shows another example of a flexible transducer assembly 530 that includes an array 500 of separate transducer piezo elements in accordance with embodiments of the present technology. The array 500 can be assembled with the flex module 204, mounted in (e.g., snapped into) the transducer frame 300 (see FIGS. 3A-3D), and the transducer frame 300 can be snapped into the base 320. This assembly can then be encased in the top shell 414 and base 320 of the patch assembly 10 as previously described. This provides an advantage of additional configurations of transducer piezo elements and scanning capabilities while using the same manufacturing/assembly processes and outer housing.

Individual piezo elements 506a-g can be mounted on one portion of the flex module 204 and piezo elements 508a-g can be mounted on another portion of the flex module 204, corresponding to the portions 216a and 216b shown in FIG. 2D, respectively. Different numbers of piezo elements 506, 508 than illustrated can be used. In some embodiments, the same sandwich construction can be used such that a layer of conductive tape 202 is used between the piezo elements 506, 508 and the flex module 204. The piezo elements 506 are held in a predetermined angular relationship (angle 224) with the piezo elements 508 as discussed previously in FIG. 2G. In this case, the angle 224 between the faces of the sets of elements is less than 180 degrees.

The transducer frame 300 can hold the flex module 204 in a convex curvature along long dimension 522, forming a curvilinear array. This results in a diverging beam and a wider imaging area, allowing less precise placement of the patch assembly 10.

The array 500 can allow for the dynamic control of beam size to insonate only tissue regions with flow. This improves energy efficiency (e.g., conserves power by turning on a subset of piezo elements 506, 508) and reduces clutter (e.g., increases SNR) from stationary tissue as well as providing a locating feature available in software control to aid the user in finding the vessel (e.g., carotid (may have more than one depth), jugular or femoral artery, use in an infant or other pediatric patient, use in bariatric patient, etc.).

Under software control, the piezo elements 506, 508 can be scanned or cycled through to identify which of the piezo elements 506, 508 are seeing flow. For example, the software may determine that piezo elements 506a and 508a are the only elements that are seeing flow. These two elements cover a scanning area 514 that includes vessel 516. The scanning area 514 may be exaggerated for illustration purposes and may be smaller and/or different than shown. The software can turn off or deactivate the piezo elements 506b-506g and 508b-508g that do not image the vessel 516 to improve or enhance the SNR. Once the piezo elements 506, 508 that are seeing flow are identified, the operation may continue as a continuous-wave transducer. Therefore, in some cases, the identified piezo elements 506, 508 can be used simultaneously as if they were a single element. This configuration can reduce energy consumption as less of the array 500 is used during normal operation. Also, SNR can be improved as less stationary tissue is insonated.

In some embodiments, the software can periodically (e.g., every minute, every five minutes, etc.) scan through all the piezo elements 506, 508 to make sure that no movement within the patient or of the patch assembly 10 has occurred.

The software can again identify the best piezo elements 506, 508 for imaging the vessel 516 and turn off the piezo elements 506, 508 that are not seeing flow.

A phased array operation may also be accomplished. In some cases, all of the piezo elements 506, 508 can be used and electronic delays between each may be used to scan the beam in a sector and locate a region of flow. Subsequently, all piezo elements 506, 508 can be used during normal operation to generate a beam focused at one particular location. The same phasing with all piezo elements 506, 508 can be used continuously to track the Doppler signal. Although energy requirements may not be reduced substantially, an improved SNR may be realized as less stationary tissue is insonated.

Figure 5B:
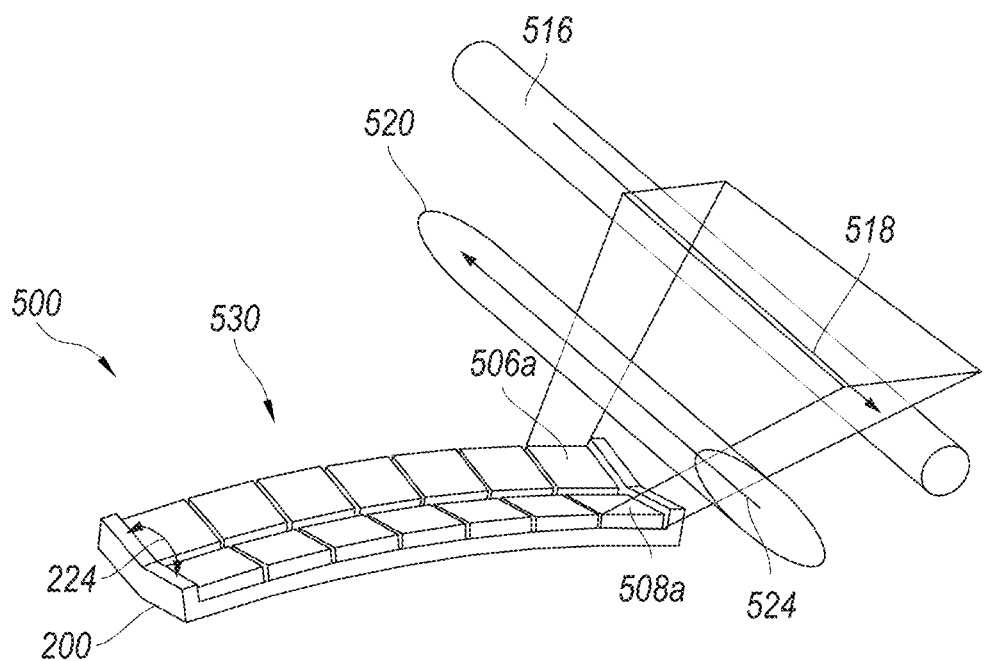
FIG. 5B shows an example of the flexible transducer assembly of FIG. 5A that is sampling vessels of opposing flow simultaneously.

FIG. 5B shows an example of the flexible transducer assembly 530 of FIG. 5A that is sampling two vessels of opposing flow simultaneously. Vessel 516 is shown with flow moving in one direction, indicated with arrow 518, while vessel 520 is shown with flow moving in another direction, indicated with arrow 524. In some embodiments, imaging the opposing flow within the vessels 516, 520 can be accomplished in spectral Doppler mode.

As shown in FIG. 5B, the vessels 516, 520 are imaged within the same scanning area 514 using the piezo elements 506a and 508a. If the vessels 516, 520 are not located within the same scanning area 514, multiple scanning areas and other piezo elements 506, 508 can be used to scan the vessels 516, 520. In some embodiments, scanning techniques can be used for enhanced imaging. For example, the Doppler power or Doppler amplitude within the jugular relates to the size of the jugular vein compared to the size of the carotid at some point and has a relationship to central venous pressure (CVP). In one embodiment, multiple Doppler amplitude or Doppler power readings for blood flowing in the jugular (reverse flow) and carotid (forward flow) are computed and stored by a processor over a cardiac cycle. Variations of more than 1.0 over a cardiac cycle may signal an increased risk for high CVP. In some embodiments, ECG signals are obtained simultaneously with the Doppler measurements to correlate the Doppler measurements with the cardiac cycle. A processor is programmed to analyze the variations in the Doppler amplitude or Doppler power over the cardiac cycle and compare against data from studies relating the Doppler amplitude and Doppler power variations to CVP. In one embodiment, the processor may store the relationship data in a memory on the ultrasound patch. In another embodiment, the processor of the ultrasound patch transmits the Doppler measurements to a remote computer over a wired or wireless link to a computer that stores the relationship data. Other scanning techniques can be used, such as is disclosed in U.S. Patent Application Publication No. 2017/0332995.

Figure 5C:
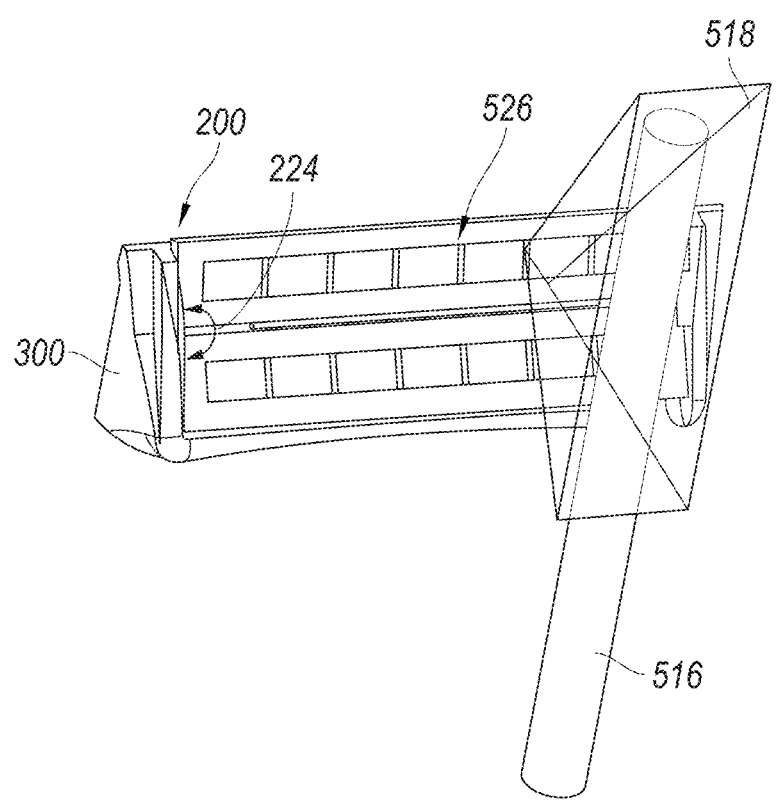
FIG. 5C shows an example of the flexible transducer assembly with an array of elements patterned on the piezo elements as discussed in connection with FIG. 2F.

FIG. 5C shows the flexible transducer assembly 200 with an array 526 of elements patterned on the piezo elements 100, as discussed previously in connection with FIG. 2F. The flexible transducer assembly 200 is held within the frame 300. As with FIGS. 5A and 5B, a subset of the array 526 may be used to scan the vessel 516 within the scanning area 514. The array 526 can be operated in continuous-wave and/or phased array as discussed herein.

In some embodiments, the ultrasound patch assembly 10 can be a continuous-wave Doppler ultrasound patch assembly that can be placed on the neck of a patient to continuously and non-invasively measure both internal jugular venous waveform velocity/morphology and Doppler power (i.e. amplitometry) in the jugular vein. This data is obtained continuously and integrated to give quantitative and qualitative assessments of the central venous pressure in a continuous and hands-free method. In some embodiments, estimates of normal, rising or high central venous pressure (CVP) rare calculated by integrating the venous velocity (VTI) over the systolic (s) and diastolic (DP phases of the heart cycle. A ratio of the systolic VTI to the sum of the systolic and diastolic VTI's is used as a guide to CVP.

In some embodiments, the software control can be provided within the patch assembly 10 and transmit data to a display on an external device, such as a smart phone or tablet. In other embodiments, the user can control the scanning mode and settings of the patch assembly 10 from the external device. Image data can be displayed on the external device, providing feedback to the user to assist with placing the patch assembly 10 on the patient. In some cases, the software can show a graphic on the screen with or without the image data to assist the user with positioning the device.

From the foregoing, it will be appreciated that specific embodiments of the invention have been described herein for purposes of illustration, but that various modifications may be made without deviating from the scope of the invention. Accordingly, the invention is not limited except as by the appended claims.

We claim:

1. An ultrasound patch assembly configured for use on the skin of a patient to detect fluid flow in a vessel in the patient, comprising:
    two piezoelectric (piezo) elements configured to transmit ultrasonic energy and detect echo signals;
    a flex module comprising first and second support portions connected to a respective one of the piezo elements, the flex module further comprising a hinged portion coupled to the first and second support portions and configured to allow the first and second support portions to be positioned angularly relative to each other, the flex module further comprising a first alignment portion;
    electronics in communication with the two piezo elements through the flex module, the electronics configured to direct the two piezo elements to transmit the ultrasonic energy, the electronics further configured to process the detected echo signals;
    a transducer frame comprising a second alignment portion that engages the first alignment portion of the flex module to retain the flex module in an aligned position on the transducer frame, the transducer frame supporting the two piezo elements at a fixed angular position with respect to each other; and
    a housing that encloses the electronics and the transducer frame within an interior area, the housing including a top surface opposite a bottom surface, the top surface configured to face away from the skin of the patient and the bottom surface configured to face toward the skin of the patient during use with the patient, wherein the housing fixedly retains the transducer frame and the flex module to position the two piezo elements to transmit the ultrasonic energy toward the bottom surface and away from the top surface.

2. The ultrasound patch assembly of claim 1, wherein active areas of the two piezo elements comprise less than an entire surface area of each of the two piezo elements.

3. The ultrasound patch assembly of claim 1, wherein portions of the two piezo elements and the flex module are electrically interconnected.

4. The ultrasound patch assembly of claim 3, wherein an anisotropic conductive tape electrically interconnects the two piezo elements and the flex module.

5. The ultrasound patch assembly of claim 1, wherein the two piezo elements each have a length and a width defining surface areas of the two piezo elements, the two piezo elements configured to have acoustically active areas that are a subset of the surface areas, wherein the acoustically active areas are surrounded by acoustically inactive areas that are positioned along outer edges of the surface areas, the flex module further comprising:
    electrodes positioned between the acoustically inactive areas of the two piezo elements and the first and second support portions; and
    anisotropic conductive tape electrically interconnecting the two piezo elements and the electrodes.

6. The ultrasound patch assembly of claim 1, wherein the fixed angular position is one of a plurality of fixed angular positions that are 180 degrees or less, the transducer frame further comprising first and second surfaces interfacing with the first and second support portions of the flex module, wherein the first and second surfaces have an angular relationship that holds the two piezo elements at the fixed angular position.

7. The ultrasound patch assembly of claim 1, wherein air gaps are formed between acoustically active areas of the two piezo elements and the flex module.

8. The ultrasound patch assembly of claim 1, wherein the housing includes a top shell and a base that are configured to be snapped together.

9. The ultrasound patch assembly of claim 1, wherein the bottom surface of the housing further comprises a central portion that protrudes outwardly to form a cavity, the transducer frame being held partially within the cavity of the housing.

10. The ultrasound patch assembly of claim 9, further comprising an acoustic medium filling at least a portion of the cavity between front surfaces of the two piezo elements and an inner surface of the cavity.

11. The ultrasound patch assembly of claim 1, wherein the first alignment portion is an opening in the flex module and the second alignment portion is a protrusion extending outwardly from a surface of the transducer frame, the protrusion extending into at least a portion of the opening when the flex module is mated with the transducer frame.

12. An ultrasound patch assembly configured for use on the skin of a patient to detect fluid flow in a vessel in the patient, comprising:
    piezoelectric (piezo) elements configured to transmit ultrasonic energy and detect echo signals, the piezo elements having front and rear surfaces;
    a flex module comprising:
        first and second support portions and a hinged portion coupled to the first and second support portions to allow the first and second support portions to be positioned angularly relative to each other;
        electrodes positioned on the first and second support portions; and
        conductive material electrically interconnecting the rear surfaces of associated ones of the piezo elements and the electrodes, wherein an air gap is formed between portions of the piezo elements and electrode-free portions of the first and second support portions;
    a transducer frame comprising:
        first and second surfaces that receive the first and second support portions of the flex module, the first and second surfaces having an angular arrangement to position the piezo elements at one of a plurality of angles relative to each other; and a retention element engaging at least one of the piezo elements to retain the first and second support portions relative to the first and second surfaces; and a housing comprising:

a top shell that has a top surface configured to face away from the skin of the patient; and a base that has a bottom surface opposite the top surface of the top shell, the bottom surface configured to face toward the skin of the patient during use with the patient, the bottom surface of the base comprising a central portion that protrudes outwardly to form a cavity within the base, the transducer frame being partially held within the cavity of the housing to position the piezo elements to transmit the ultrasonic energy toward the bottom surface and away from the top surface.

13. The ultrasound patch assembly of claim 12, wherein the bottom surface forms a wedge corresponding to the cavity that includes a wedge face, the piezo elements configured to transmit the ultrasound energy and detect the echo signals through the wedge face.

14. The ultrasound patch assembly of claim 13, wherein the wedge further having a back side that is smaller than the wedge face.

15. The ultrasound patch assembly of claim 12, further comprising:

a first alignment feature associated with the flex module; and a second alignment feature associated with the transducer frame, the first and second alignment features interfacing with each other to maintain alignment of the flex module relative to the transducer frame.

16. The ultrasound patch assembly of claim 12, wherein the angular arrangement of the first and second surfaces of the transducer frame is determined based on an imaging depth.

17. The ultrasound patch assembly of claim 12, wherein the transducer frame includes sidewalls that extend outwardly from the first and second surfaces, the sidewalls and first and second surfaces forming a receiving area for the first and second support portions and the piezo elements, the retention element protruding from the sidewalls into the receiving area.

18. The ultrasound patch assembly of claim 12, wherein the first and second support portions are made of a rigid material.

* * * * *